(12) United States Patent
O'Brien et al.

(10) Patent No.: US 9,138,483 B2
(45) Date of Patent: *Sep. 22, 2015

(54) COLLAGEN/HYDROXYAPATITE COMPOSITE SCAFFOLD, AND PROCESS FOR THE PRODUCTION THEREOF

(71) Applicant: ROYAL COLLEGE OF SURGEONS IN IRELAND, Dublin (IE)

(72) Inventors: Fergal Joseph O'Brien, Dublin (IE); John Patrick Gleeson, Dublin (IE); Niamh Plunkett, Dublin (IE)

(73) Assignee: ROYAL COLLEGE OF SURGEONS IN IRELAND, Dublin (IE)

( * ) Notice: Subject to any disclaimer, the term of this patent is extended or adjusted under 35 U.S.C. 154(b) by 268 days.

This patent is subject to a terminal disclaimer.

(21) Appl. No.: 13/786,891

(22) Filed: Mar. 6, 2013

(65) Prior Publication Data

US 2013/0177648 A1 Jul. 11, 2013

Related U.S. Application Data

(63) Continuation of application No. 12/526,353, filed as application No. PCT/IE2008/000010 on Feb. 11, 2008, now Pat. No. 8,435,552.

(30) Foreign Application Priority Data

Feb. 9, 2007 (EP) .................... 07394001

(51) Int. Cl.
| | | |
|---|---|---|
| A61K 47/42 | (2006.01) | |
| A61K 47/02 | (2006.01) | |
| A61L 27/46 | (2006.01) | |
| A61L 27/56 | (2006.01) | |

(52) U.S. Cl.
CPC ............... *A61K 47/42* (2013.01); *A61K 47/02* (2013.01); *A61L 27/46* (2013.01); *A61L 27/56* (2013.01)

(58) Field of Classification Search
CPC ........ A61K 47/42; A61K 47/02; A61L 27/46; A61L 27/56
See application file for complete search history.

(56) References Cited

U.S. PATENT DOCUMENTS

| | | | |
|---|---|---|---|
| 6,180,606 B1 | 1/2001 | Chen et al. | |
| 6,201,039 B1 | 3/2001 | Brown et al. | |
| 6,626,950 B2 | 9/2003 | Brown et al. | |
| 6,730,252 B1 * | 5/2004 | Teoh et al. ............... | 264/178 F |
| 6,946,443 B2 | 9/2005 | Blanchat et al. | |
| 7,494,664 B2 | 2/2009 | Sotome et al. | |
| 7,732,573 B2 | 6/2010 | Tanaka et al. | |
| 8,008,357 B2 | 8/2011 | Shoji et al. | |
| 8,039,090 B2 | 10/2011 | Kawamura et al. | |
| 2003/0180270 A1 | 9/2003 | Simon | |
| 2005/0107286 A1 | 5/2005 | Uemura et al. | |
| 2006/0172918 A1 | 8/2006 | Sotome et al. | |
| 2007/0088437 A1 | 4/2007 | Betz et al. | |
| 2007/0166348 A1 | 7/2007 | Van Dyke | |
| 2008/0241211 A1 | 10/2008 | Han et al. | |
| 2008/0242850 A1 | 10/2008 | Kim et al. | |
| 2008/0281431 A1 | 11/2008 | Missos | |
| 2009/0017093 A1 | 1/2009 | Springer et al. | |
| 2010/0036503 A1 | 2/2010 | Chen et al. | |
| 2010/0080777 A1 | 4/2010 | Giannini et al. | |
| 2010/0267143 A1 | 10/2010 | Park et al. | |
| 2010/0297210 A1 | 11/2010 | Okihana | |
| 2011/0014266 A1 | 1/2011 | Shoji | |
| 2011/0033552 A1 | 2/2011 | Shoji | |
| 2011/0059178 A1 | 3/2011 | Semler et al. | |
| 2011/0217388 A1 | 9/2011 | Greenspan et al. | |
| 2011/0256203 A1 | 10/2011 | Kim et al. | |
| 2011/0262486 A1 | 10/2011 | Tsai et al. | |
| 2012/0015003 A1 | 1/2012 | Gleeson et al. | |
| 2012/0114763 A1 | 5/2012 | Kim et al. | |

FOREIGN PATENT DOCUMENTS

| | | |
|---|---|---|
| BR | WO 2011/150482 A1 | 12/2011 |
| EP | 0 855 884 B1 | 6/2004 |
| EP | 1437148 | 7/2004 |
| EP | 1 447 104 A1 | 8/2004 |
| EP | 1500405 | 1/2005 |
| EP | 1566186 | 8/2005 |
| EP | 1 270 025 B1 | 5/2006 |
| EP | 1 275 405 B1 | 10/2006 |
| EP | 1 858 562 B1 | 11/2009 |
| GB | WO 2005/051147 A1 | 6/2005 |

(Continued)

OTHER PUBLICATIONS

Ducheyne, P. et al. "The effect of calcium phosphate ceramic composition and structure on in vitro behavior. I. Dissolution," J. of Biomed. Materials Research, 27:25-34 (1993).

(Continued)

*Primary Examiner* — Robert A Wax
*Assistant Examiner* — William Craigo
(74) *Attorney, Agent, or Firm* — Nixon Peabody LLP

(57) ABSTRACT

A process for producing a collagen/hydroxyapatite (HA) composite scaffold comprises the steps of forming a homogenous suspension of collagen and HA in an acidic solution, lyophilizing the suspension until a desired final freezing temperature is reached to produce the composite scaffold, and optionally cross-linking the composite scaffold, wherein the ratio of HA to collagen is at least 1:10 (w/w). Also provided is a collagen/hydroxyapatite (HA) composite scaffold comprising a homogenous distribution of hydroxyapatite within a porous, crosslinked, collagen matrix, wherein the ratio of HA to collagen is at least 1:10 (w/w). Suitably, the composite scaffold has a porosity of at least 99% (v/v), and a compressive stiffness of at least 0.3 KPa. Composite scaffolds of the invention may be used to provide osteoconductive bone implants and tissue engineering implants.

15 Claims, 21 Drawing Sheets

(56) References Cited

FOREIGN PATENT DOCUMENTS

| GB | WO 2006/095154 A2 | 9/2006 |
|---|---|---|
| GB | WO 2008/017858 A2 | 2/2008 |
| KR | WO 2008/130068 A1 | 10/2008 |
| WO | 2005/004928 | 1/2005 |
| WO | 2006/031196 | 3/2006 |
| WO | WO 2008/157608 A1 | 12/2008 |
| WO | WO 2011/030185 A1 | 3/2011 |
| WO | WO 2012068376 A2 | 5/2012 |

OTHER PUBLICATIONS

Higashi, T. et al. "Influence of Particle Size of Hydroxyapatite as a Capping Agent on Cell Proliferation of Cultured Fibroblasts," J. of Endodontics, 22(5):236-239 (1996).

Kikuchi, M. et al. "Biomimetic synthesis of bone-like nanocomposites using the self-organization mechanism of hydroxyapatite and collagen," Composites Science and Technology 64:819-825 (2004).

Nadra, I. et al. "Effect of particle size on hydroxyapatite crystal-induced tumor necrosis factor alpha secretion by macrophages," Atherosclerosis 196:98-105 (2008).

Rouahi, M. et al. "Influence of hydroxyapatite microstructure on human bone cell response," J. of Biomedical Materials Research Part A DOI 10.11002/jbma.a (2006) Wiley InterScience (www.interscience.wiley.com).

Stulajterova, R. et al. "Effect of calcium ions on transformation brushite to hydroxyapatite in aqueous solutions," Colloids and Surfaces A: Physiochem. Eng. Aspects 316:104-109 (2008).

Supova, M. "Problem of hydroxyapatite dispersion in polymer matrices: a review," J. Mater Sci: Mater Med 20:1201-1213 (2009).

Taqvi, S. et al. "Influence of scaffold physical properties and stromal cell coculture on hematopoietic differentiation of mouse embryonic stem cells," Biomaterials 27:6024-6031 (2006).

Ter Brugge, P.J. et al. "Effect of calcium phosphate coating crystallinity and implant surface roughness on differentiation of rat bone marrow cells," J. Biomed. Mater. Res. 60:70-78 (2002).

Wu, T. et al. "Studies on the microspheres comprised of reconstituted collagen and hydroxyapatite," Biomaterialsls 25:651-658 (2004).

Database WPI Week 200480 Thomson Scientific, London, GB; AN 2004-805630 XP 002440997 & CN 1526765 Biomedical Eng Inst Chinese Acad Medical; Sep. 8, 2004, abstract.

O'Brien et al., Biomaterials, 25(6):1077-1086 (2004). "Influence of freezing rate on pore structure in freeze-dried collagen-GAG scaffolds."

Bailey et al., Chemical Cross-linking Restrictions on Models for the Molecular Organization of the Collagen Fibre. Nature, 288:408-410 (1980).

Dong et al., "Heat-Pressed Ceramics: Technology and Strength." International Journal of Prosthodontics, 5(1):9-16 (1992).

O'Brien et al., "The Effect of Pore Size on Cell Adhesion in Collagen-GAG Scaffolds." Biomaterials, 26:433-441 (2005).

O'Brien et al., "The Effect of Pore Size on Permeability and Cell Attachment in Collagen Scaffolds for Tissue Engineering." Technology and Healthcare Invited Article, 15:3-17 (2007).

Tancred et al., "Development of a new synthetic bone graft." Journal of Materials Science: Materials in Medicine, 9 (12):819-823 (1998).

* cited by examiner

COLLAGEN/HYDROXYAPATITE COMPOSITE SCAFFOLD, AND PROCESS FOR THE PRODUCTION THEREOF

CROSS REFERENCE TO RELATED APPLICATIONS

This application is a continuation of U.S. patent application Ser. No. 12/526,353, filed on Feb. 4, 2010, which is a 371 National Phase Entry Application International Application No. PCT/IE2008/000010 filed Feb. 11, 2008, which designated the U.S., and claims the benefit of European Application No. 07394001.7 filed Feb. 9, 2007.

TECHNICAL FIELD

The invention relates to a process for producing a collagen/hydroxyapatite (HA) composite scaffold, and collagen/HA composite scaffolds obtainable by the process of the invention. Such scaffolds may be used in bone regeneration and tissue engineering applications.

BACKGROUND ART

Bone grafts are second only to blood transfusions on the list of transplanted materials worldwide. In addition, the estimated worldwide market for bone graft material is about £650 million each year. Every year, up to 4 million bone replacement procedures are performed worldwide which require the use of a bone graft or scaffold. The most common clinical treatment is an autograft whereby bone is taken from the patient's own body and reimplanted. However there is a limited amount of bone which can be removed from a particular donor site and additional invasive surgery is required for reimplantation. Another option is the use of an allograft whereby bone is removed from an organ donor. Problems with this approach stem from the origin of the bone from a separate donor. A higher risk of infectious disease transmission is associated with such material. In addition, fewer growth factors are present in such donor bone because it contains no living cells. These growth factors aid the growth of new bone. An ideal implantable scaffold that would promote bone formation while facilitating load bearing would reduce the need for allografts or autografts. However, presently these traditional approaches constitute over 90% of all bone graft procedures. The reason for this shortfall, despite the problems described above, is that a vascularised, mechanically competent, osteoconductive scaffold that could be used to produce bone in vitro or cause complete osteogenesis in vivo remains to be developed. Such a product would have significant commercial potential.

Various attempts have been made using numerous synthetic materials to produce viable scaffolds for bone grafting. Examples include polystyrene, titanium, polyllactic acid (PLLA), polyglycolic acid (PGA) and polylacticcoglycolic acid (PLGA). However, all these materials have associated problems and drawbacks including the risk of infection and difficulties allowing adequate resorption to promote vascularisation and ingrowth of new bone. Biological materials such as collagen, gelatin, chitosan, agarose and glycosaminoglycan (GAG) based substrates have also been used. However these materials do not have mechanical properties sufficient to allow load bearing after implantation.

STATEMENTS OF INVENTION

According to the invention, there is provided a process for producing a collagen/hydroxyapatite (HA) composite scaffold, comprising the steps of forming a homogenous suspension of collagen and HA in an acidic solution, lyophilising the suspension until a desired final freezing temperature is reached to produce the composite scaffold, and optionally cross-linking the composite scaffold, wherein the ratio of HA to collagen in the suspension is at least 1:10 (w/w).

Typically, the acidic solution has a molarity of at least 0.05M. In a preferred embodiment of the invention, the ratio of HA to collagen in the suspension is greater than 1:10 (w/w), and wherein the molarity of the acidic solution is greater than 0.05M. Typically, the ratio of HA to collagen in the suspension is at least 2:10 (w/w), 3:10 (w/w), 4:10 (w/w), 5:10 (w/w). In one preferred embodiment of the invention the ratio of HA to collagen is from 1:10 (w/w) to 50:10 (w/w), suitably from 5:10 (w/w) to 30:10 (w/w). Suitably, the molarity of the acidic solution is at least 0.06M, 0.07M, 0.08M, 0.09M, 0.10M, 0.20M, 0.30M, 0.40M, or 0.50M. Ideally, the molarity of the acidic solution is between 0.4M and 0.6M.

In one preferred embodiment of the invention, the ratio of HA to collagen in the suspension is at least 5:10 (w/w), and wherein the molarity of the acidic solution is at least 0.10M. Typically, the molarity of the acidic solution is at least 0.50M.

In a preferred embodiment of the invention, the ratio of HA to collagen in the suspension is at least 6:10 (w/w), 7:10 (w/w), 8:10 (w/w), 9:10 (w/w), or 1:1 (w/w). In one embodiment of the invention, the ratio of HA to collagen in the suspension is greater than 1:1 (w/w). Generally, when such levels of HA are employed in the suspension, the molarity of the acidic solution will be at least 0.5M.

In a preferred embodiment, the amount of collagen in the suspension can vary from 0.5 g/L up to 50 g/L of acid solution (1/10 and 10 times standard collagen concentration respectively). Suitably, the amount of collagen in the suspension is between 1.0 g/L and 10.0 g/L, preferably between 3.0 g/L and 8.0 g/L, and more preferably between 4.0 g/L and 6.0 g/L.

Typically, the acidic solution comprises an acetic acid solution. However, other organic acids may be employed to form the acidic solution.

Suitably, the homogenous suspension of collagen/HA is formed in conditions suitable for minimising gelatinisation of the collagen. One method of ensuring minimal gelatinisation of collagen during the production of the homogenous suspension is to maintain the suspension at a sufficiently low temperature, generally between 1° and 5° C., suitably about 4° C.

In one embodiment of the invention, lyophilisation is carried out at a constant cooling rate. This means that the rate of cooling during the lyophilisation does not vary by more than +/−10% of the target cooling rate, i.e. if the desired rate of cooling is 1.0° C./min, and the actual rate of cooling varied between 0.9° C./min and 1.1° C./min, this would nonetheless still be considered to be a constant cooling rate. Typically, the constant cooling rate is between 0.1° C./min to 10° C./min. Preferably, lyophilisation is carried out at a constant cooling rate of between 0.5° C./min to 1.5° C./min. More preferably, lyophilisation is carried out at a constant cooling rate of between 0.8° C./min to 1.1° C./min. Typically, lyophilisation is carried at a constant cooling rate of about 0.9° C./min. The temperature of the lyophilisation chamber at a start of the lyophilisation process (i.e. when the slurry is placed in the chamber) is usually greater than 0° C., preferably at about ambient temperature.

In one embodiment, the desired final freezing temperature is between −10° C. and −70° C. Suitably, the desired final freezing temperature is between −30° C. and −50° C. Typically, the desired final freezing temperature is between −35° C. and −45° C., ideally about −40° C.

The lyophilisation process generally includes a drying stage, which is carried out after the final freezing temperature is reached. This step involves heating the lyophilisation chamber to a sublimation temperature (generally about 0° C.), preferably at a constant heating rate. The process typically includes a final sublimation step where an ice phase in the formed scaffold is sublimated under vacuum for a suitable period of time.

In another embodiment of the invention, the lyophilisation process comprises an annealing step. Typically, this step involves increasing the temperature in the lyophilisation chamber after the final freezing temperature has been reached, and typically holding the increased temperature for a period of time before initiating the drying stage. For example, if the final freezing temperature is −20° C., the annealing step may be carried out by ramping up the temperature to −10° C., and holding at that temperature for a time sufficient to allow existing ice crystals grow, before finally drying the scaffold. The annealing time may be varied according to the pore characteristics desired, however annealing times of between 15 minutes and 120 hours are preferred.

Generally, the HA employed in the present invention is in powder form. Suitably, the HA powder is selected from the group comprising: sintered HA powder; and unsintered HA powder. Examples of suitable sintered, and unsintered, HA powders suitable for the present invention will be known to the person skilled in the art, and are provided below.

Typically, the HA powder has a particle size of between 10 μm and 100 μm.

Suitably, the collagen employed in the present invention comprises collagen fibres. Preferably, the collagen fibres comprise microfibrillar collagen, preferably microfibrillar bovine tendon collagen.

In one embodiment of the invention, the homogenous suspension of collagen/HA is formed by the steps of:
  forming an acidic homogenous suspension of collagen; and
  subsequently adding the HA to the collagen suspension under conditions of mixing to ensure homogenous distribution of the HA within the collagen suspension.

Preferably, the HA is provided in the form of an acidic HA suspension. Suitably, the collagen suspension is centrifugally mixed, and wherein the HA is added to the vortex of the suspension during centrifugal mixing.

Typically, the HA is added in aliquots. Suitably, the aliquots are added to the collagen suspension at intervals of between 30 and 240 minutes. Preferably, the HA is added to the collagen suspension in between 2 and 5 aliquots.

In one embodiment of the invention, the composite scaffold is cross-linked. Typically, the composite scaffold is cross-linked by a means selected from the group comprising: dehydrothermal cross-linking; and chemical cross-linking. Suitable chemical cross-linking agents and methods will be well known to those skilled in the art and include 1-Ethyl-3-[3-dimethylaminopropyl]carbodiimide hydrochloride (EDAC). When dehydrothermal cross-linking is employed, the cross-linking temperature is between 105° C. and 180° C. Suitably, the cross-linking process is carried for at least 24 hours, 48 hours, 72 hours, 96 hours, or 120 hours. When EDAC crosslinking is employed, the molarity of the EDAC solution is 6 mmol per gram of collagen/HA composite The invention also relates to a collagen/hydroxyapatite (HA) composite scaffold obtainable by the method of the invention.

The invention also relates to a collagen/hydroxyapatite (HA) composite scaffold comprising a homogenous distribution of hydroxyapatite within a porous, collagen matrix, wherein the ratio of HA to collagen is at least about 1:10 (w/w).

Preferably, the composite scaffold of the invention has a porosity of at least 95% (v/v), 96% (v/v), 97% (v/v), 98% (v/v), 99% (v/v, 99.1% (v/v), 99.2% (v/v), 99.3% (v/v). Suitably, the composite scaffold of the invention has a porosity of from 97% to 99.5% (v/v), preferably from 98 to 99.5% (v/v), and more preferably from 98.5 to 99.5% (v/v). The method of determining % porosity is described below.

Suitably, composite scaffold of the invention has a compressive stiffness of at least 0.2 KPa, 0.3 KPa, 0.4 KPa, 0.5 KPa, 0.6 KPa. Suitably, the composite scaffold of the invention has a compressive stiffness of from 1 to 5 KPa, preferably from 1 to 4 KPa. EDAC crosslinked composite scaffolds have a compressive stiffness of at least 1 kPa, 1.5 kPa, 2 kPa, 2.5 kPa, 3 kPa, 3.5 kPa, 4 kPa. The method of determining compressive stiffness is described below.

Typically, the ratio of HA to collagen in the composite scaffold is from 1:10 to 50:10 (w/w), and preferably at least 2:10 (w/w), 3:10 (w/w), 4:10 (w/w), 5:10 (w/w), 6:10 (w/w), 7:10 (w/w), 8:10 (w/w), 9:10 (w/w), or 1:1 (w/w). In a particularly preferred embodiment of the invention, the ratio of HA to collagen in the composite scaffold is from 5:10 to 30:10 (w/w).

The in vitro bioactivity of the composite scaffold of the invention may be characterised by monitoring the activity of MC3T3 osteoblasts in the scaffold after 1 day (to monitor the degree of initial cellular attachment) 7 day, 21 day and 28 days incubation (to monitor cellular proliferation). In one embodiment of the invention, the composite scaffold of the invention is characterised by a level of proliferation of MC3T3 osteoblasts in the scaffold after 7 days incubation of greater than the initial number of cells seeded onto the scaffold. Typically this is at least $1 \times 10^6$ cells per 500 mm$^3$ volume of scaffold. In a preferred embodiment of the invention, the composite scaffold is characterised by a level of proliferation of MC3T3 osteoblasts in the scaffold at 28 days incubation minus the level at 7 days of at least $0.5 \times 10^6$ cells, and suitably from $0.5 \times 10^6$ and $1.5 \times 10^6$ cells A method for determining the level of proliferation of MC3T3 osteoblasts is as follows: A cylindrical sample of composite scaffold of diameter 12.7 mm is seeded with $2 \times 10^6$ MC3T3 cells. After 7 days of incubation, the number of cells present per scaffold is monitored using the Hoechst 33258 DNA assay. This gives an assessment of initial cell attachment. After 14, 21 and 28 days of incubation, the number of cells present per scaffold is monitored using the Hoechst 33258 DNA assay. The change in number of cells present per scaffold over time (number of cells at day 28 minus number of cells at day 7) is used to assess cellular proliferation.

In one embodiment, the composite scaffold of the invention is characterised by having a flow conductivity under pressure through the scaffold of at least $1 \times 10^{-10}$ m$^4$/Ns., suitably from $6 \times 10^{-10}$ m$^4$/Ns to $1.4 \times 10^{-9}$ m$^4$/Ns, preferably from $8 \times 10^{-10}$ m$^4$/Ns to $1.2 \times 10^{-9}$ m$^4$/Ns. Typically, the flow conductivity under pressure through the scaffold is at least $10 \times 10^{-10}$ m$^4$/Ns.

Ideally, the composite scaffold of the invention has a high degree of pore interconnectivity. Preferably, the scaffold has a homogenous pore distribution. Typically, the scaffold has a homogenous pore size. In one embodiment, the scaffold is produced in the form of a sheet. Typically, the sheet has an average thickness of at least 1 mm, 2 mm, 3 mm, 4 mm, 5 mm, 6 mm, 7 mm, 8 mm, 9 mm or 10 mm.

The invention also relates to a composite scaffold of the invention, or obtainable by a method of the invention, that is seeded with cells. Typically, the cells are stem cells that are undifferentiated, partially differentiated, or fully differentiated. In one embodiment, the cells are selected from the group consisting of: osteoblasts; and mesenchymal stem cells.

The invention also relates to a osteoconductive bone implant comprising a composite scaffold according to the invention.

The invention also relates to a tissue engineering implant comprising a composite scaffold according to the invention. Thus, the scaffold of the invention may form a base upon which tissue may be engineered. Various forms of tissue are envisaged for this application, including but not limited to, cartilage, ligaments, muscle, and organs.

The invention also relates to a maxillofacial bone graft substitute comprising a composite scaffold according to the invention.

The invention also relates to a dental bone graft substitute comprising a composite scaffold according to the invention.

The invention also relates to a cartilage defect repair implant comprising a composite scaffold according to the invention.

The invention also relates to an osteochondral defect repair implant comprising a composite scaffold according to the invention.

The proposed invention is produced from the two primary constituents of bone, namely the mineral phase, hydroxyapatite (HA) and the organic phase, collagen. As such, it is a more natural substrate than any of the materials previously described that promotes bone formation. Furthermore, by combining the high mechanical stiffness of HA with the biocompatability, biodegradability and pore architecture of a collagen scaffold manufactured using the specific process of the invention, a product which has all the criteria required for use as an osteoconductive scaffold has been developed, including excellent compressive stiffness (to facilitate handling and in vivo loading), and a high degree of porosity, pore interconnectivity, and permeability.

Hydroxyapatite is a ceramic material. Ceramics are inorganic, nonmetallic compounds that form ionic and covalent bonds. They are characterised by high mechanical stiffness, very low elasticity and a hard, brittle surface. In living tissue, HA combines with collagen to form the primary constituents of bone. As a material it also exhibits both a chemical and crystal resemblance to bone mineral. However, pure HA constructs are unattractive for a number of reasons, most notably the rigidity, brittle nature and poor resorbability of the material [1]. Consequently, stability and control of construct degradation rate is problematic [2], severely inhibiting optimal resorption, subsequent tissue ingrowth and restoration of the mechanical integrity of the defect site, all of which are significant determinants of successful implantation.

In contrast to HA, the second constituent of the present invention, collagen, already fulfills all the biological determinants required for successful implantation. It is a natural polymer present in numerous tissues throughout the human body, therefore exhibiting excellent biocompatability. As a result collagen promotes cell adhesion, proliferation and extracellular matrix (ECM) formation. Its degradation rate can be controlled in vivo by varying the crosslink density. Crosslinks are chemical bonds between collagen molecules. They provide the mechanical strength of collagen and stabilise the collagen fibres by preventing the long rodlike collagen molecules from sliding past each other under stress [3]. Crosslinking is also an effective means of controlling the degradation rate of collagen scaffolds, as the crosslinks have to be broken down before the scaffold can be degraded. There are various methods of increasing the level of crosslinking in collagen scaffolds. Another significant attribute is the recent FDA approval and clinical success of collagen-based scaffolds used for skin and nerve regeneration [4]. The major drawback associated with collagen as a scaffold is its lack of inherent mechanical strength. Consequently, this invention combines both collagen and HA to form a composite three-dimensional construct with the advantages of both constituents and none of the disadvantages.

In addition to the actual constituent materials themselves, the scaffold fabrication process and subsequent morphology of the construct is vital in determining in vivo success of the scaffold implant. Manufacture of the present invention involves the use of a specialised collagen scaffold fabrication technique that typically includes lyophilisation/freezedrying. Traditionally, the manufacture of porous scaffolds using lyophilisation involved the rapid freezing or quenching of the constituent scaffold materials blended together in a slurry. This results in an extremely irregular pore distribution and large degree of pore size variation. Additionally, quenching alters the aspect ratio of the created pores, leading to nonequiaxed pore shapes throughout. The freezedrying manufacturing process of the present invention facilitates comprehensive control of all main morphological determinants of scaffold viability. It does so by precisely controlling the temperature and pressure within the freezedrying chamber during both the freezing and drying stages of the process. Uncontrolled freezing or drying at any point during the manufacturing process has been shown to lead to heterogeneous pore distributions, shapes and sizes, all of which are vital determinants of seeded-cell viability. Using a controlled freezedrying process, porous, reproducible and homogenous collagen based scaffolds can be repeatedly manufactured with high pore interconnectivity, porosity and surface area, all of which are vital for successful mass transport of cells within the scaffold and surrounding host tissue and provide space for vascularisation and ingrowth of new tissue. Additionally, the method of the invention allows extensive control of construct pore size, facilitating cell-specific functionality. The present disclosure describes the fabrication of a composite scaffold, through the use of the process of the invention that results in a porous, three dimensional scaffold having high porosity, high pore interconnectivity, and a homogenous distribution of HA within the collagen matrix.

HA=Non-EDAC crosslinked scaffold collagen +200 wt % HA mixed in 0.5M acetic acid).

Figure 4:
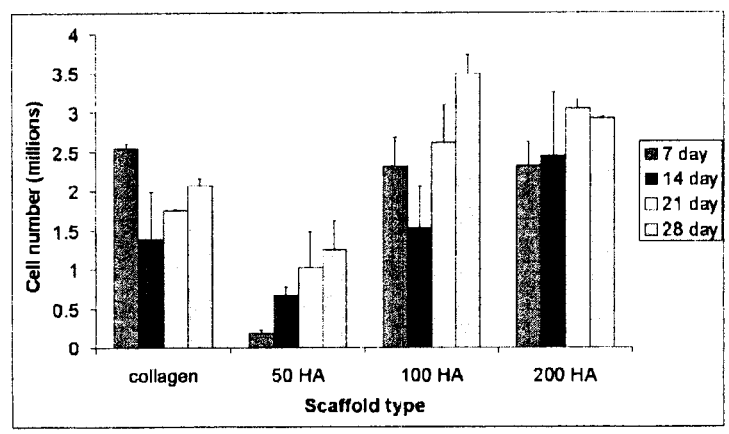

FIG. 4: In-vitro bioactivity as a function of scaffold type (t=7, 14, 21, 28 days) Initial seeding density of 2 million cells used on all scaffolds. (collagen=EDAC crosslinked collagen control scaffold mixed in 0.5M acetic acid, 50 HA=EDAC crosslinked collagen+50 wt % HA mixed in 0.5M acetic acid, 100 HA=EDAC crosslinked collagen+100 wt % HA mixed in 0.5M acetic acid, 200 HA=EDAC crosslinked collagen+200 wt % HA mixed in 0.5M acetic acid).

Figure 5:
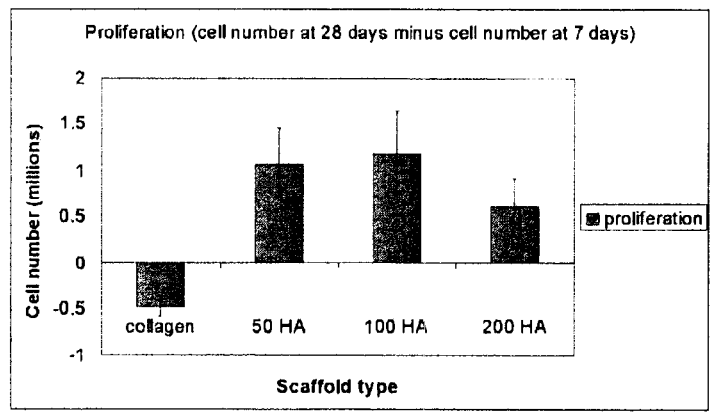

FIG. 5: In-vitro bioactivity as a function of scaffold type (t=28 days–7 days) New bioactivity of scaffolds between day 7 and day 28 (collagen=EDAC crosslinked collagen control scaffold mixed in 0.5M acetic acid, 50 HA=EDAC crosslinked collagen+50 wt % HA mixed in 0.5M acetic acid, 100 HA=EDAC crosslinked collagen+100 wt % HA mixed in 0.5M acetic acid, 200 HA=EDAC crosslinked collagen+200 wt % HA mixed in 0.5M acetic acid).

Figure 6:
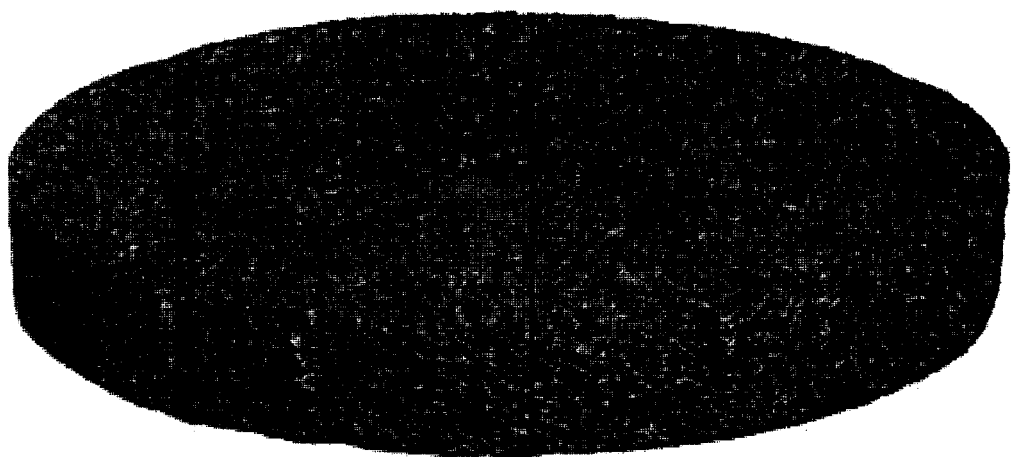

FIG. 6: MicroCT scan of composite scaffold according to the invention.

Figure 7:
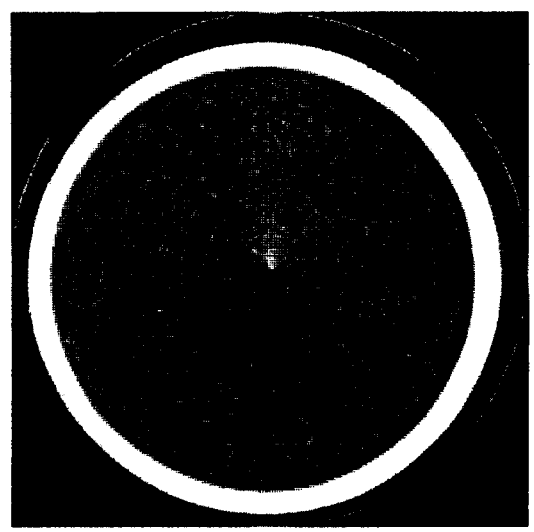

FIG. 7: Section of scaffold of FIG. 6.

Figure 8:
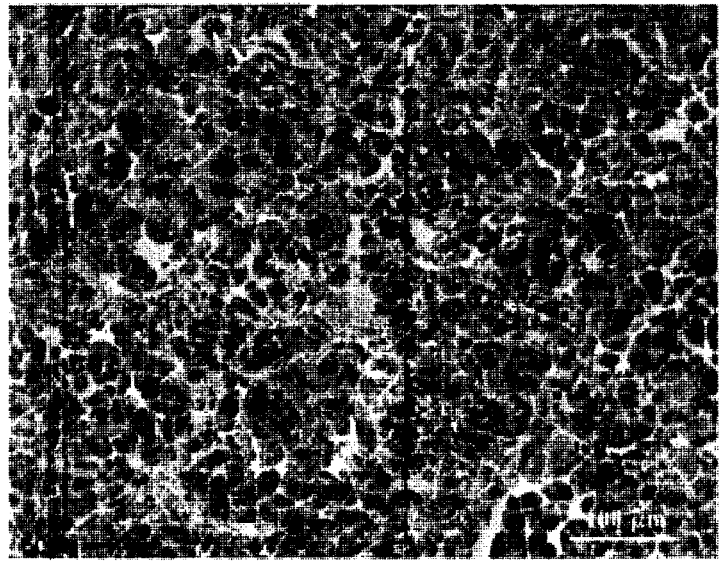

FIG. 8: 50 wt % HA scaffold SEM image highlighting homogenous and interconnected pore structure.

Figure 9:

FIG. 9: Mineral particle distribution of region of interest defined in FIG. 8.

Figure 10:
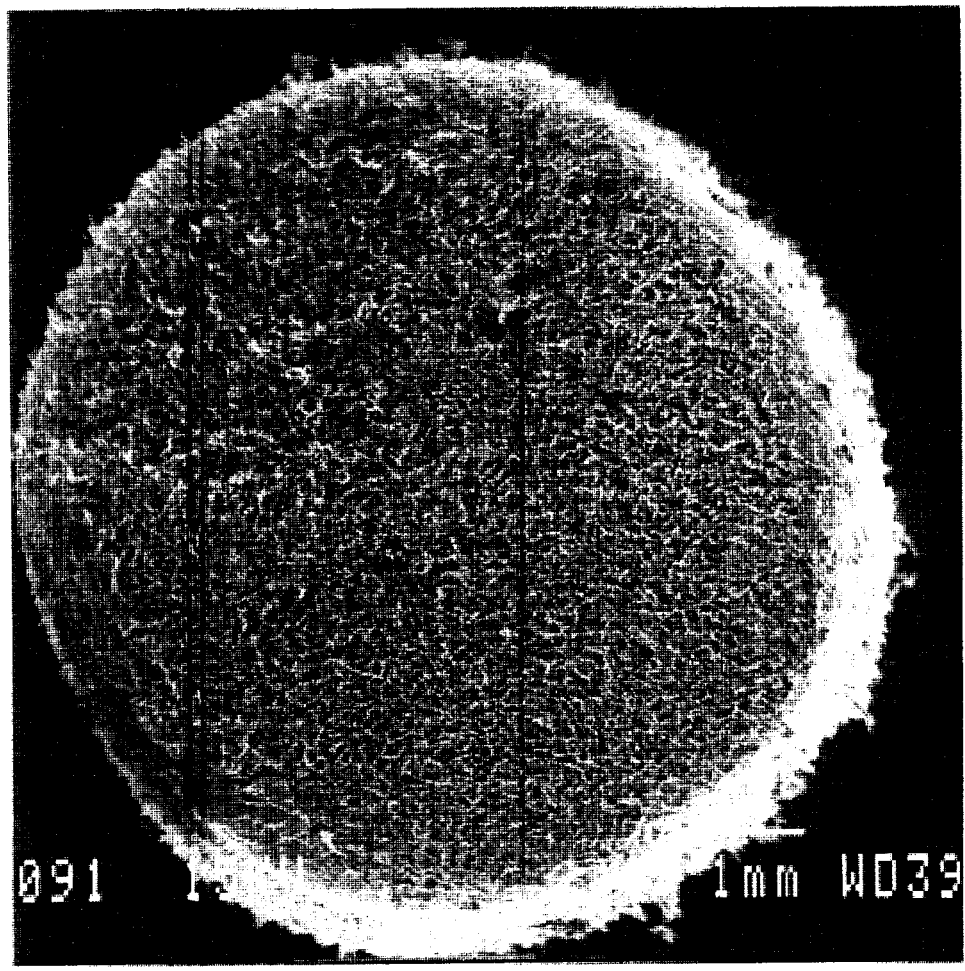
Figure 11:
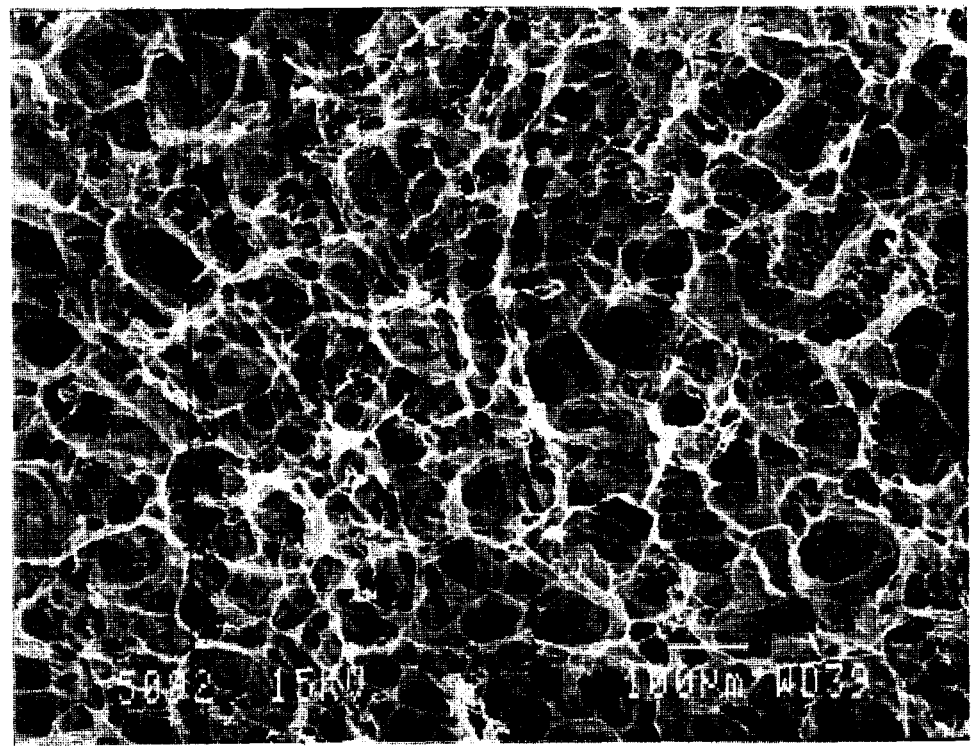

FIGS. 10 and 11: SEM images of a non-EDAC crosslinked 50 wt % HA composite scaffold according at 10 times and 100 times magnification respectively.

Figure 12:
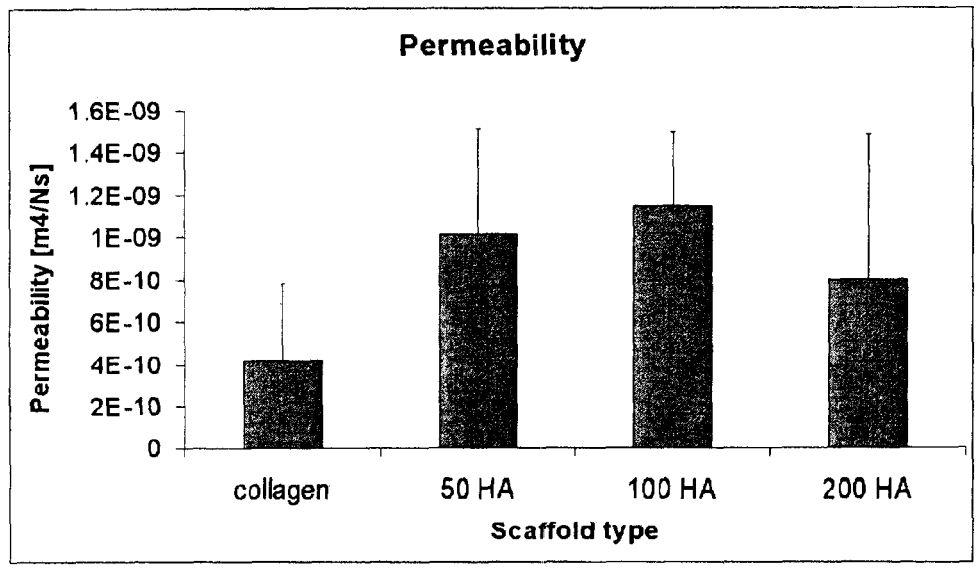

FIG. 12: Scaffold permeability as a function of scaffold type. (collagen=EDAC crosslinked collagen control scaffold mixed in 0.5M acetic acid, 50 HA=EDAC crosslinked collagen+50 wt % HA mixed in 0.5M acetic acid, 100 HA=EDAC crosslinked collagen+100 wt % HA mixed in 0.5M acetic acid, 200 HA=EDAC crosslinked collagen+200 wt % HA mixed in 0.5M acetic acid).

Figure 13:
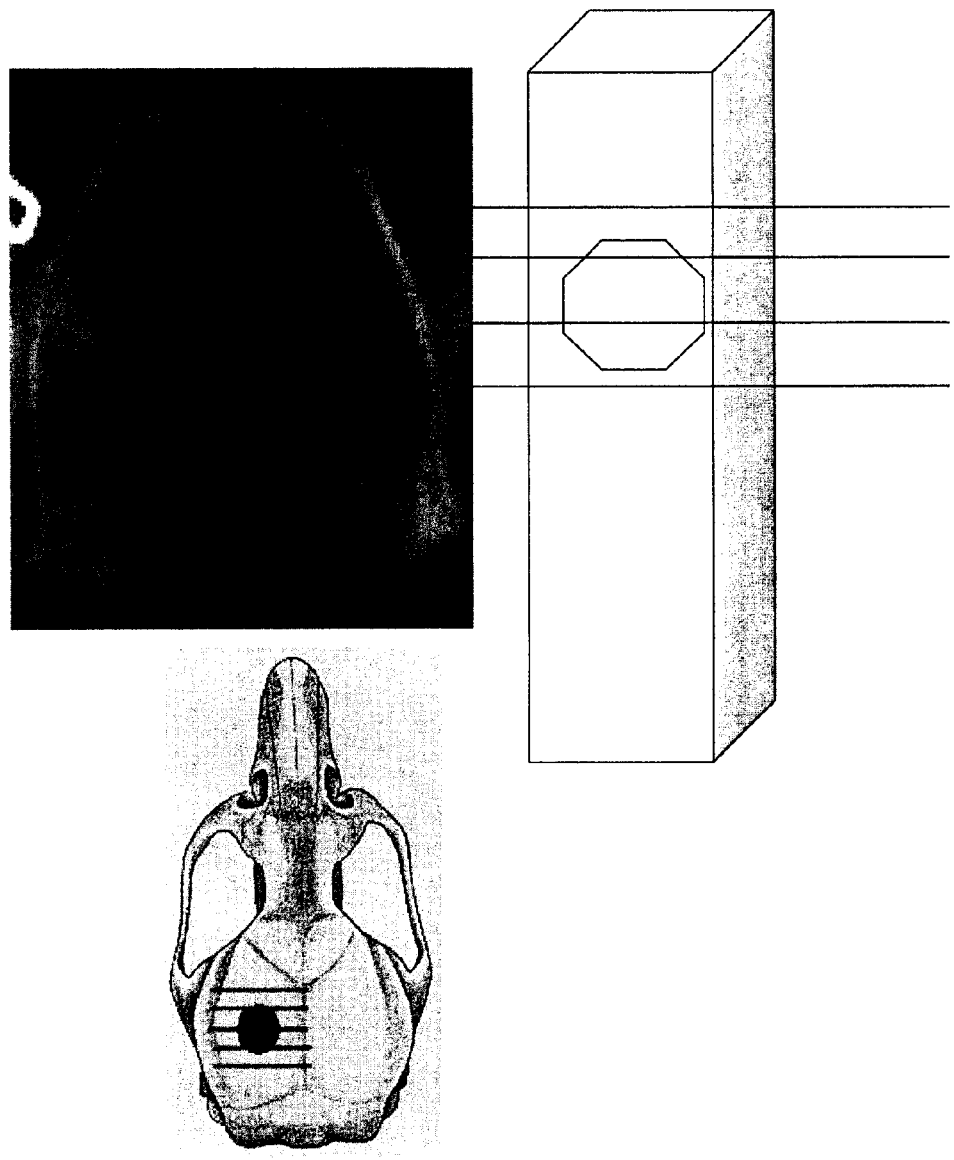

FIG. 13: X-ray of a rat calvarial bone and accompanying schematic showing the position of the defect and the positions of the sections taken for the CT Scan images.

Figure 14:
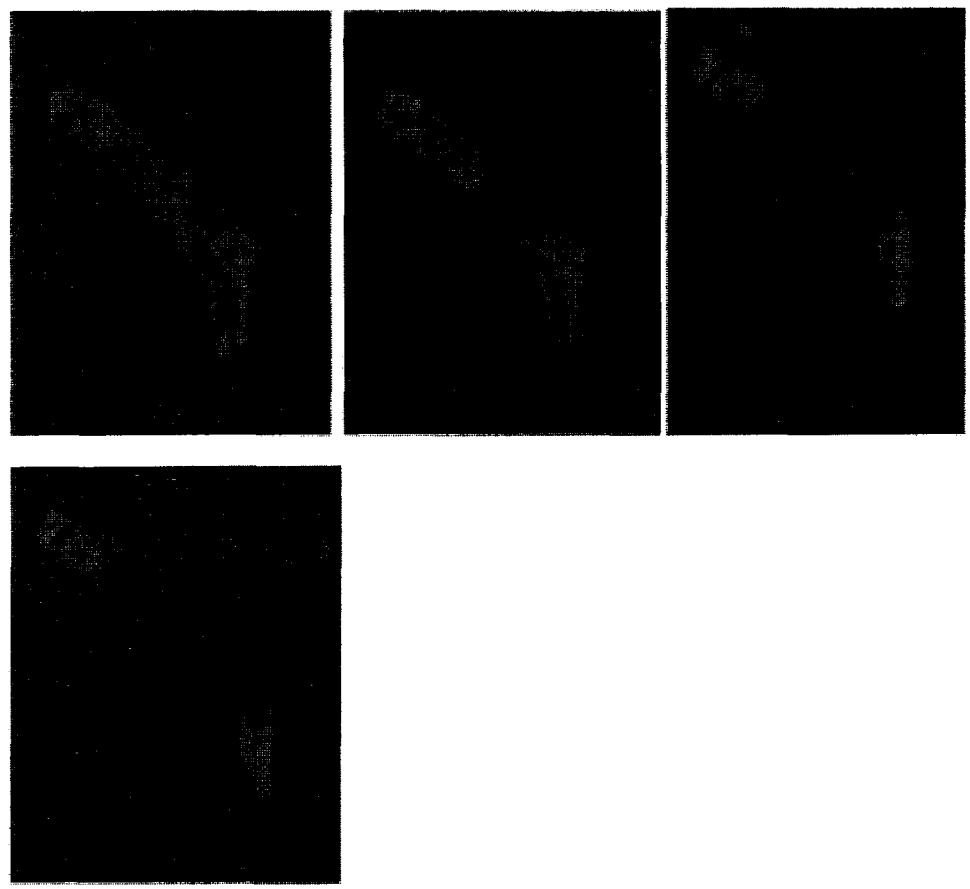

FIG. 14: MicroCT scan images of sections of a rat calvarial bone having an empty defect.

Figure 15:
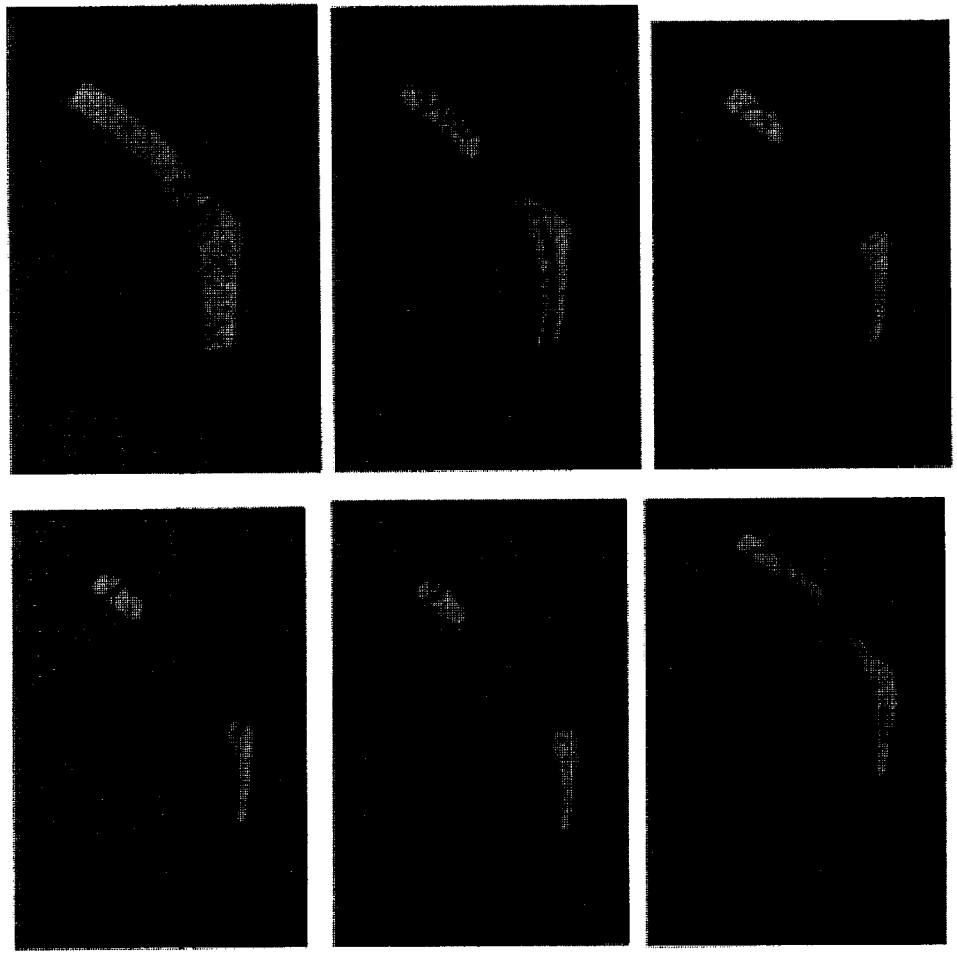
Figure 16:
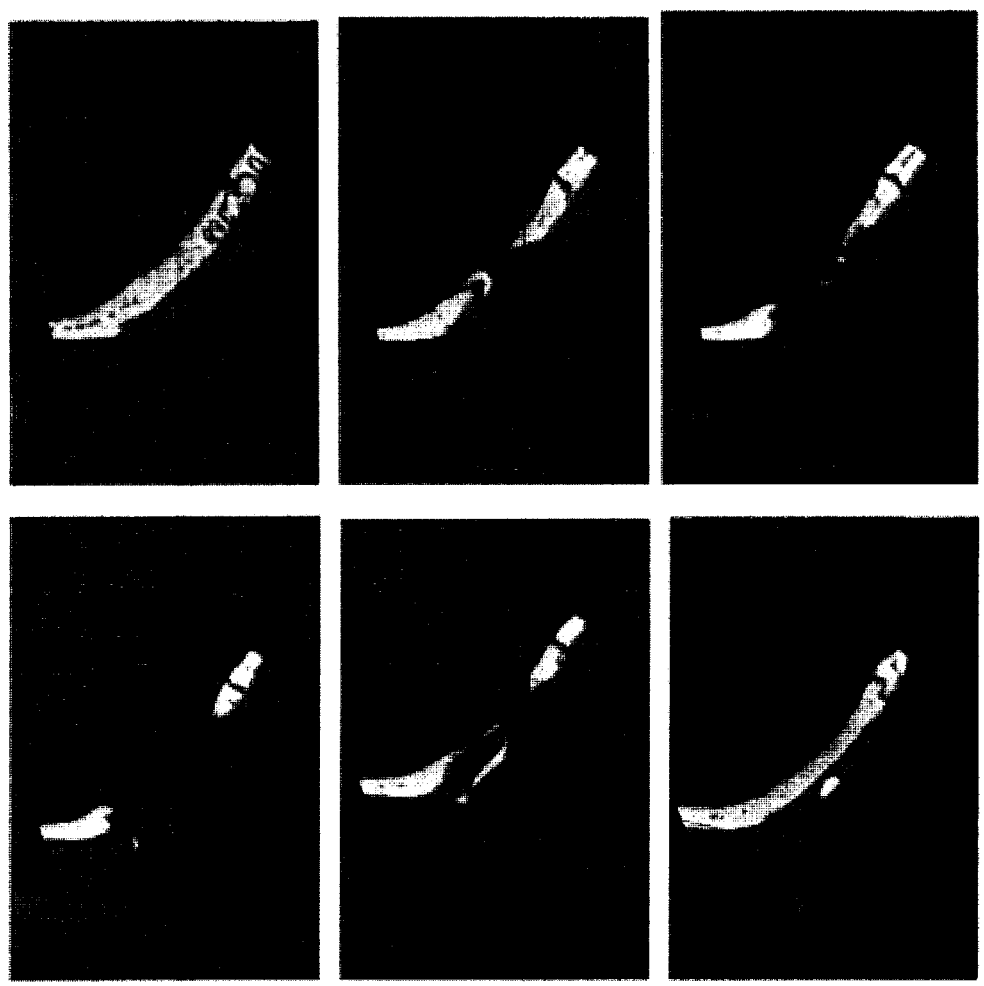

FIGS. 15 and 16: MicroCT scan images of sections of a rat calvarial bone having a defect filled with a EDAC crosslinked 50 wt % HA composite scaffold of the invention seeded with rat MSC cells.

Figure 17:
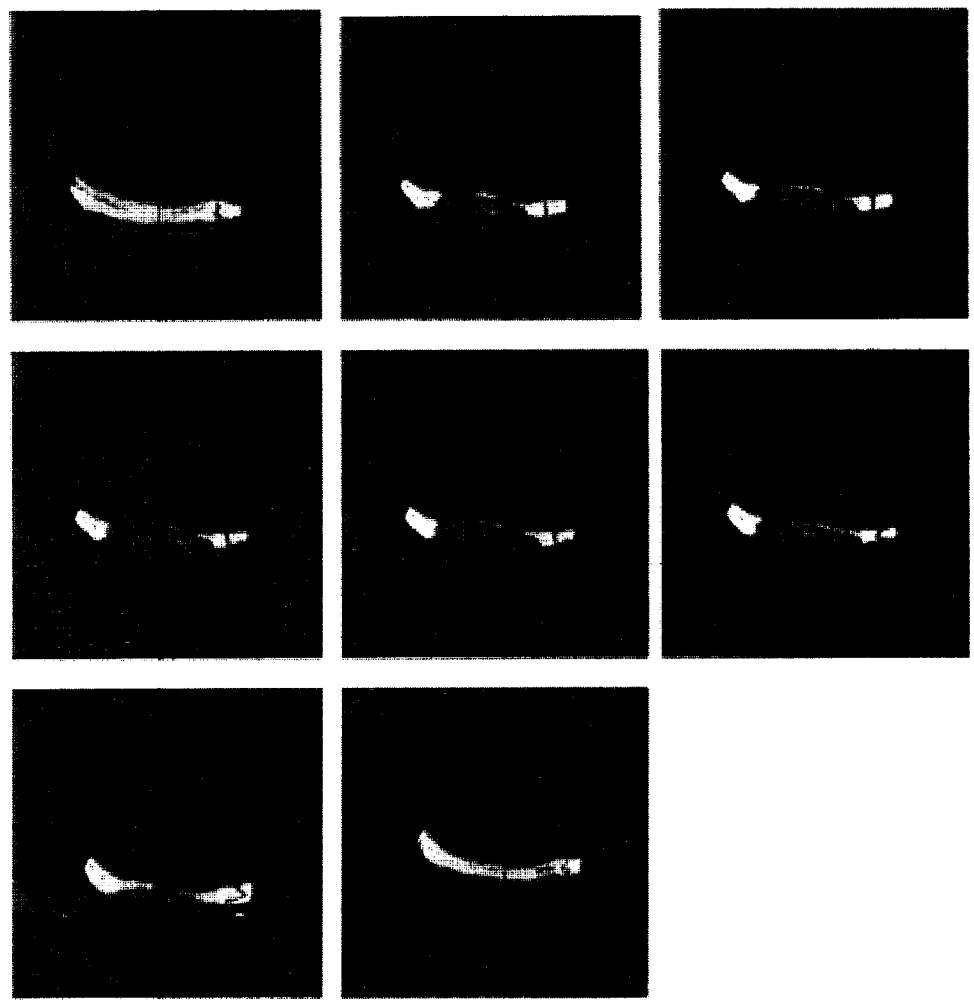
Figure 18:
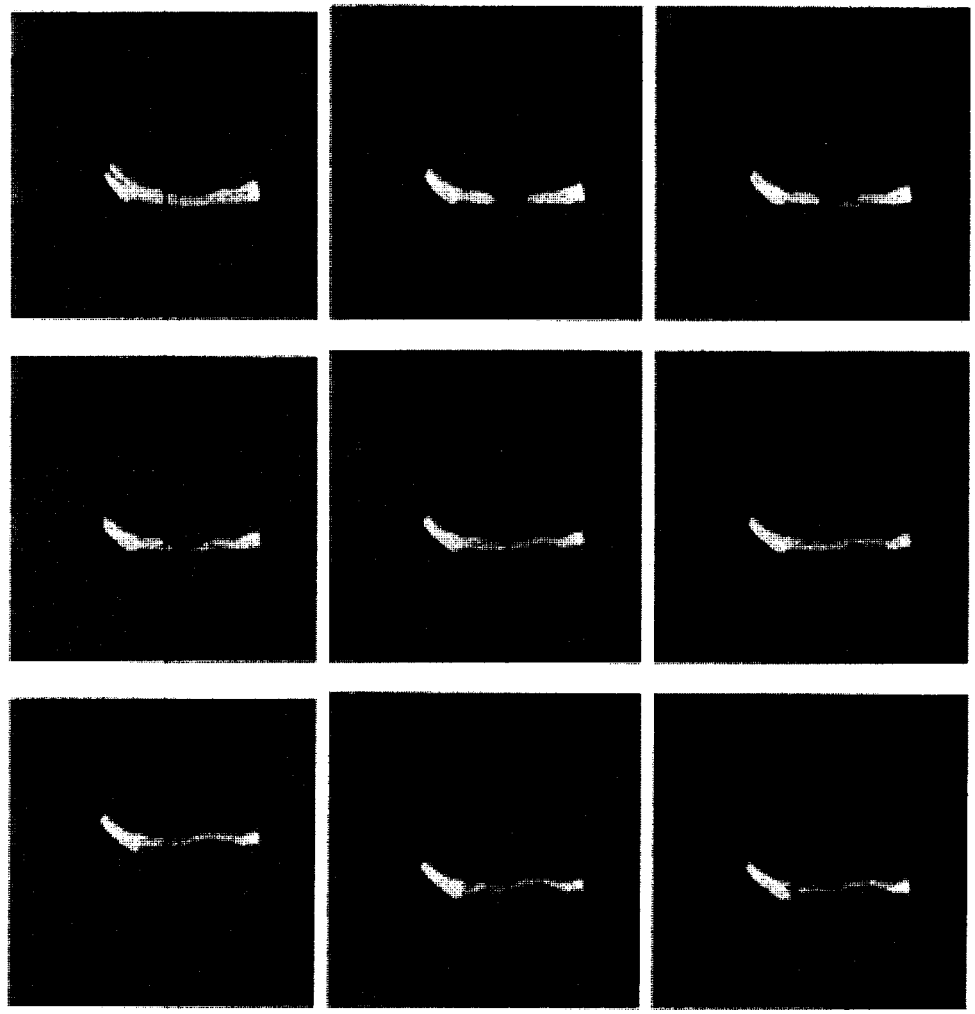
Figure 18:
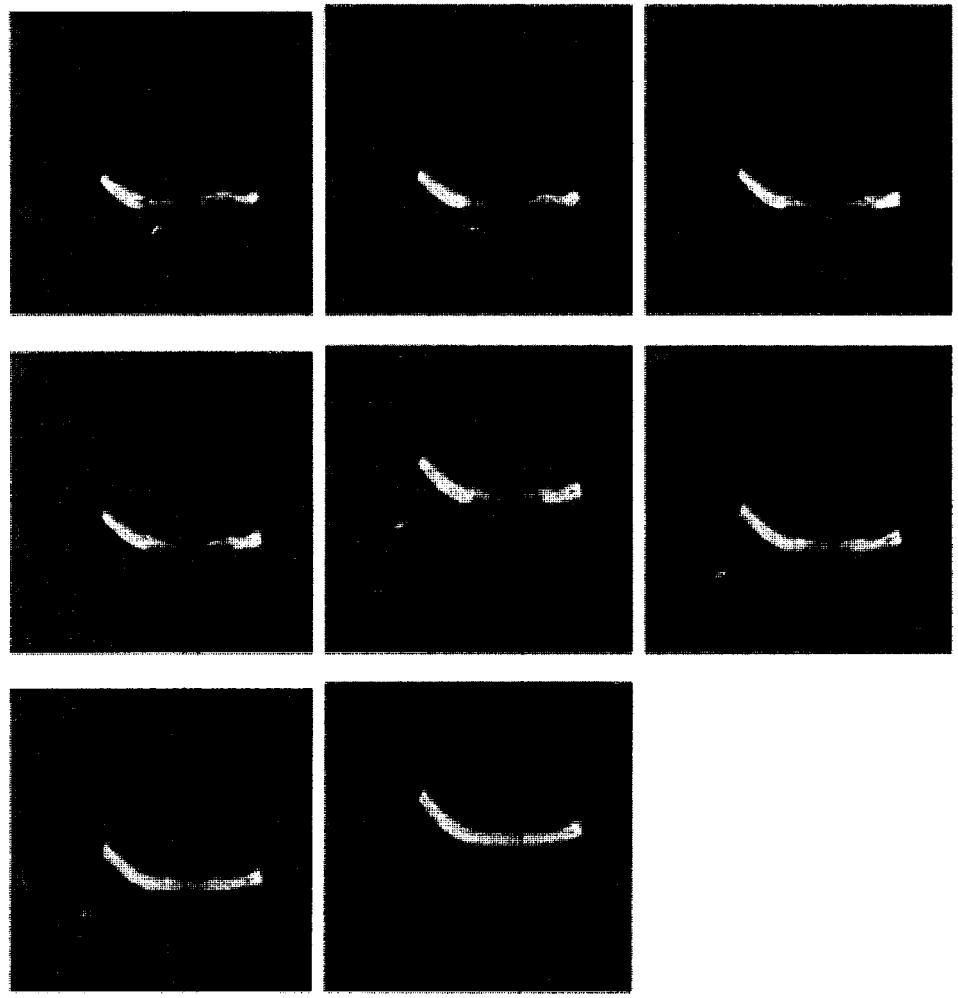

FIGS. 17 and 18: MicroCT scan images of sections of a rat calvarial bone having a defect filled with a EDAC crosslinked 200 wt % HA composite scaffold of the invention seeded with rat MSC cells.

Figure 19:
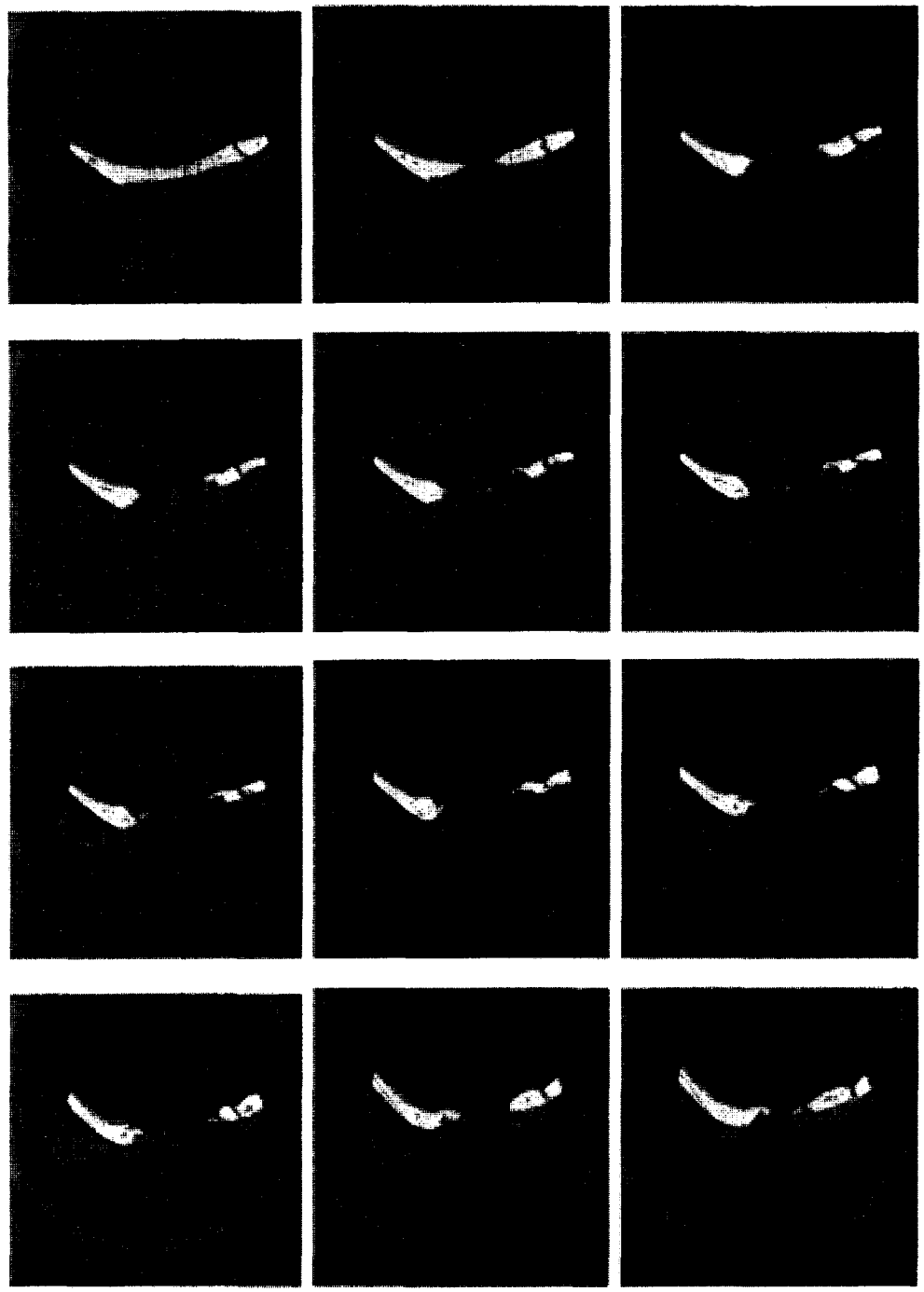
Figure 19:
Figure 20:
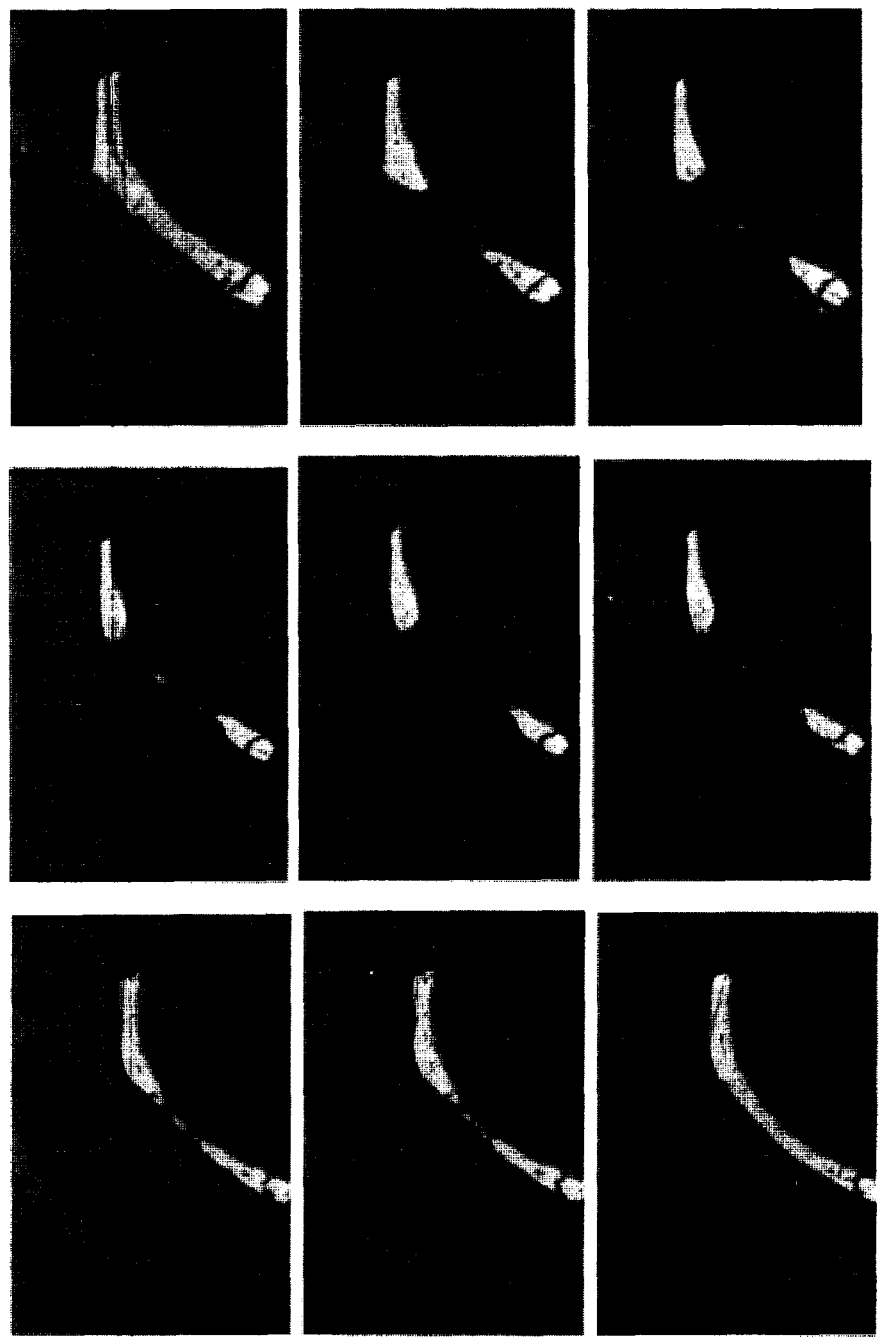

FIGS. 19 and 20: MicroCT scan images of sections of a rat calvarial bone having a defect filled with a EDAC crosslinked 50 wt % HA composite scaffold of the invention (unseeded).

Figure 21:
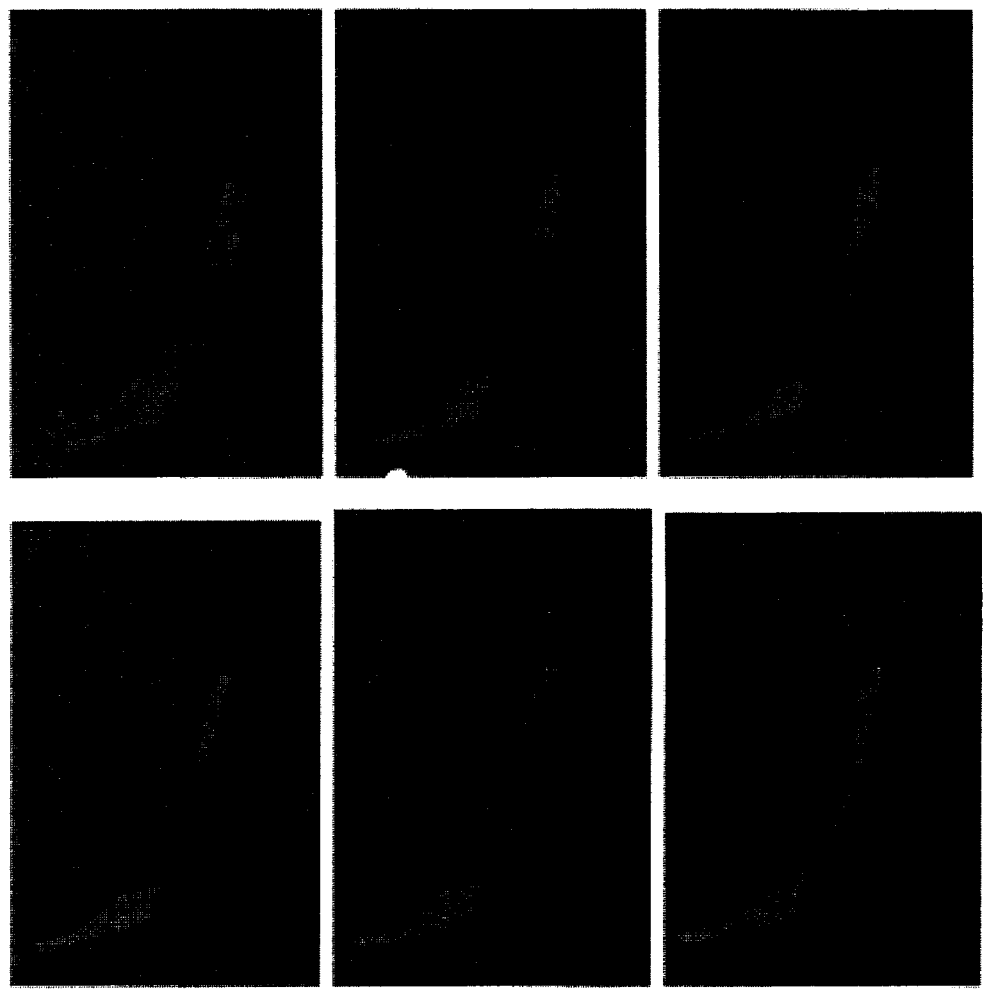
Figure 21:
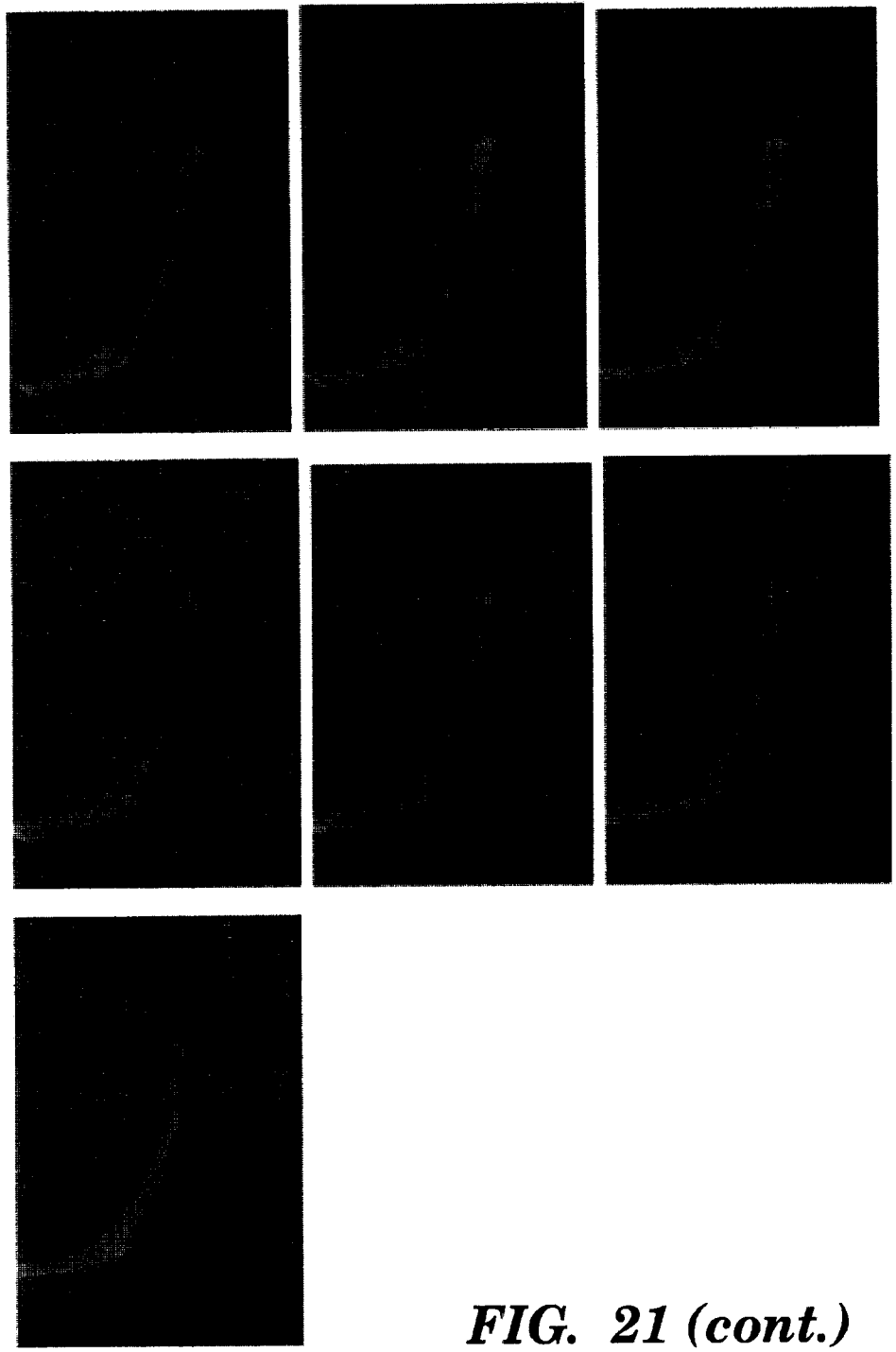
Figure 22:
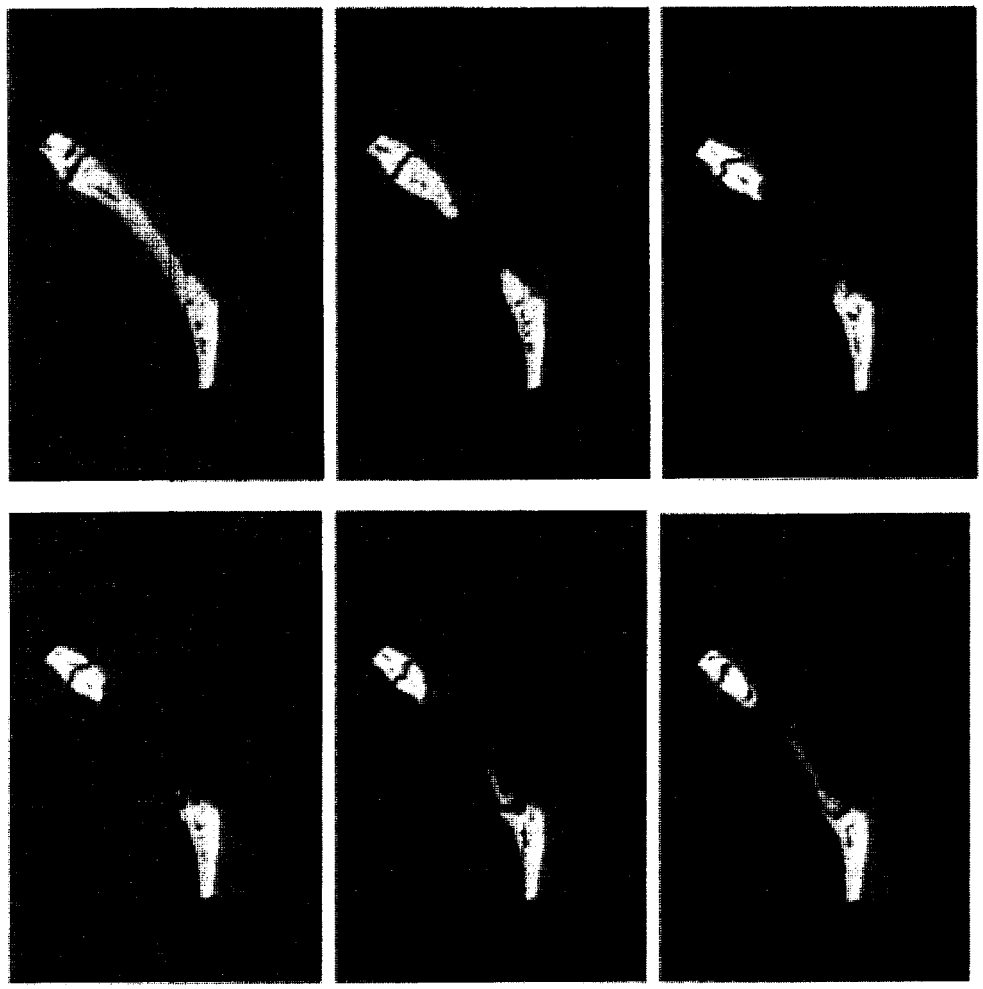
Figure 22:
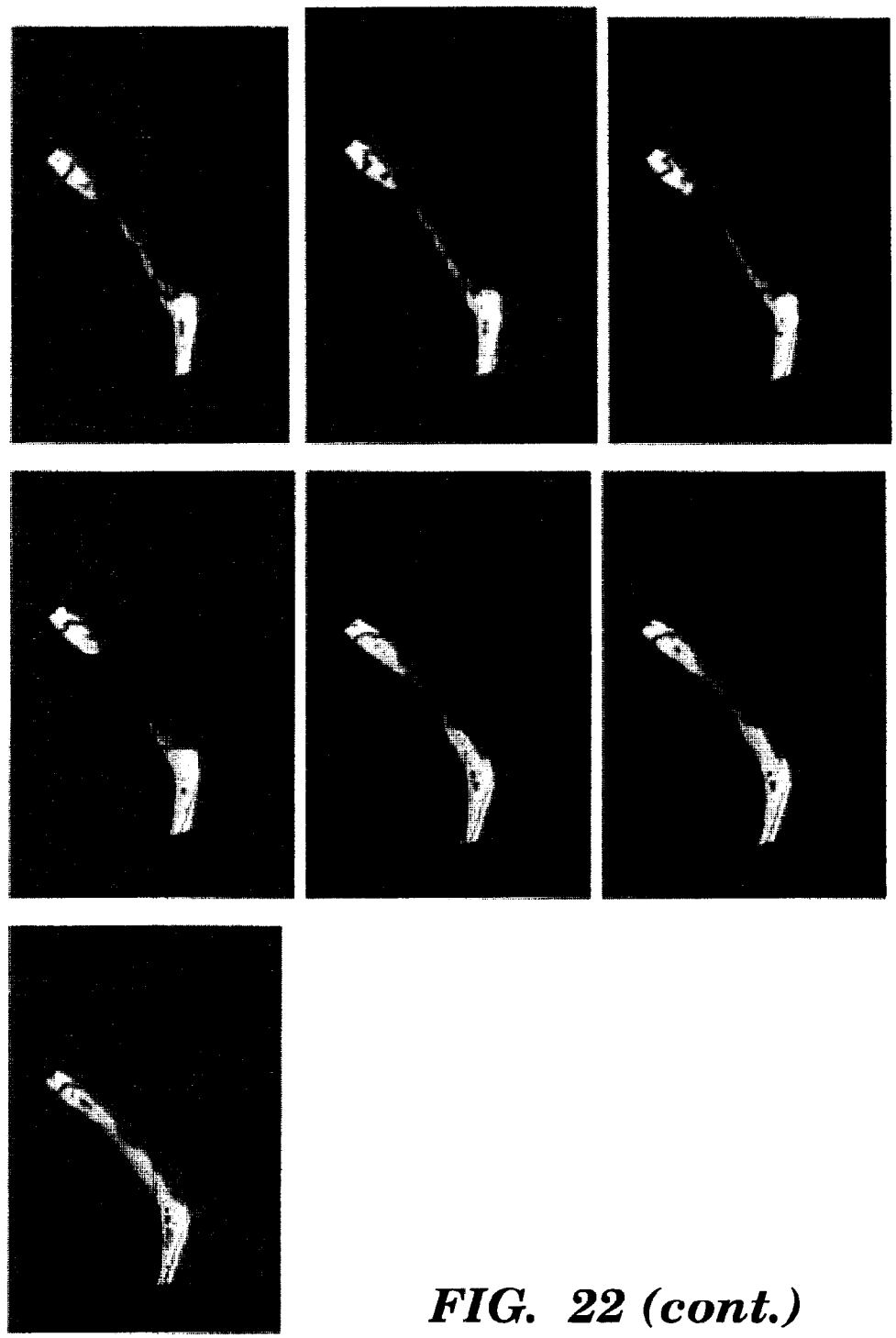

FIGS. 21 and 22: CT scan images of sections of a rat calvarial bone having a defect filled with a EDAC crosslinked 200 wt % HA composite scaffold of the invention (unseeded).

DETAILED DESCRIPTION OF THE INVENTION

Fabrication of the Invention collagen control scaffolds and 10 wt % HA scaffolds were manufactured using the protocol described in Embodiment 1, specifically using an initial acetic acid concentration of 0.05M. As the proportion of HA was increased up to 50 wt % HA, homogenous mixing of the two main constituents (collagen and HA) became more problematic. An increase in the initial acetic acid concentration was found to alleviate this problem. The effect of this increased acetic acid concentration was investigated using two distinct increases in acetic acid concentration, specifically 0.1M and 0.5M. These embodiments are described in Examples 2 and 3, respectively. The manufacture of EDAC crosslinked collagen control scaffolds and composite scaffolds having 50 wt %, 100 wt %, and 200 wt % HA, are described in Example 4.

Example 1

400 ml of a 0.05 M acetic acid solution (pH 3.05) was prepared using distilled, deionised water (1.16 ml glacial acetic acid was added to 398.84 ml of distilled, deionized water).

A WK1250 water cooling system (Lauda, Westbury, N.Y., USA) was used to cool a glass reaction vessel to a constant temperature of 4° C. for one hour. This reaction vessel was used to blend the scaffold constituents while maintaining the slurry at a constant temperature of 4° C. This prevented denaturation of the collagen fibres as a result of heat generation during the blending process.

1.8 gm of microfibrillar bovine tendon collagen (Collagen Matrix Inc., N.J., USA) was added to 320 ml of the 0.05 M acetic acid solution. This suspension was blended using an IKA Ultra Turrax T18 overhead blender (IKA Works Inc., Wilmington, N.C.) at 15,000 rpm for 90 minutes at 4° C. 40 ml of the acetic acid solution was mixed with hydroxyapatite (HA) powder (Biotal, UK), specifically 10% by weight of collagen (0.18 gm HA). A 10 ml aliquot of this acetic acid/HA solution was added to the collagen/acetic acid slurry in the cooled reaction vessel at 90 minutes. The method of HA suspension delivery involved a vigourous shaking of the suspension immediately prior to injection (ensuring a homogenous suspension of the mineral particles) into the blender vortex centre via syringe. A flexible rubber tube was attached to the syringe nozzle to facilitate injection directly into the blender vortex centre. 10 ml aliquots (three in total) were added subsequently to the slurry every hour. After the final aliquot of acetic acid HA solution was added, the slurry was blended for a subsequent 60 minutes, leading to a total blend time of 330 minutes (five and a half hours).

Once the blending stage was completed, the slurry was transferred to a clean, widenecked beaker and vacuum degassed at a pressure of approximately 4000 mTorr for an additional 60 minutes. This stage removed any unwanted air bubbles within the slurry as this would have a detrimental effect on the subsequent freezedrying process. The scaffold was produced using a lyophilisation (freezedrying) process. A 67.5 ml aliquot of the collagen/HA slurry was placed in a walled freezedryer sample tray supplied by the freezedryer manufacturer (VirTis Co., Gardiner, N.Y., USA) and made from 304 grade stainless steel. The inner sample tray dimensions were 127 mm wide×127 mm length×38 mm height. The tray base plate thickness is 3 mm. The sample tray was placed into the freezedryer chamber and placed on the freezedryer cooling shelf at a temperature of 20° C.

The freezedrying process involved the cooling of the freezedryer chamber and cooling shelf at a constant cooling rate (0.9° C./min), based on a previous study, to the final temperature of freezing (40° C.). The primary determinant of ice crystal morphology during the freezedrying process is the final temperature of freezing. The shelf and chamber temperature was then held constant at the final temperature of freezing for 60 minutes to complete the freezing process. The shelf temperature was then ramped up to 0° C. over 160 minutes. The ice phase was then sublimated under a vacuum of approximately 200 mTorr at 0° C. for 17 hours to produce the porous collagen/HA scaffold.

The porous collagen/HA construct was then placed in a vacuum oven (Fisher IsoTemp 201, Fisher Scientific, Boston, Mass.) to crosslink the collagen via a dehydrothermal crosslinking process. The scaffolds were placed in the vacuum oven at a temperature of 120° C. under a vacuum of 50 mTorr for 24 hours.

Example 2

400 ml of a 0.1 M acetic acid solution (pH 2.9) was prepared using distilled, deionised water (2.32 ml glacial acetic acid was added to 397.68 ml of distilled, deionized water). A WK1250 water cooling system (Lauda, Westbury, N.Y., USA) was used to cool a glass reaction vessel to a constant temperature of 4° C. for one hour. 1.8 gm of microfibrillar bovine tendon collagen (Collagen Matrix Inc., N.J., USA) was added to 320 ml of the 0.1 M acetic acid solution. This suspension was blended using an IKA Ultra Turrax T18 overhead blender (IKA Works Inc., Wilmington, N.C.) at 15,000 rpm for 90 minutes at 4° C.

40 ml of the acetic acid solution was mixed with hydroxyapatite (HA) powder (Biotal, UK), specifically 50% by weight of collagen (0.9 gm HA). A 10 ml aliquot of this acetic acid/HA solution was added to the collagen/acetic acid slurry in the cooled reaction vessel at 90 minutes. 10 ml aliquots (three in total) were added subsequently to the slurry every hour. After the final aliquot of acetic acid HA solution was added, the slurry was blended for a subsequent 60 minutes, leading to a total blend time of 330 minutes (five and a half hours). Once the blending stage was completed, the slurry was transferred to a clean, widenecked beaker and vacuum degassed at a pressure of approximately 4000 mTorr for an additional 60 minutes.

The scaffold was produced using a lyophilisation (freezedrying) process. A 67.5 ml aliquot of the collagen/HA slurry was placed in a walled freezedryer sample tray supplied by the freezedryer manufacturer (VirTis Co., Gardiner, N.Y., USA) and made from 304 grade stainless steel. The inner sample tray dimensions were 127 mm wide×127 mm length× 38 mm height. The tray base plate thickness is 3 mm. The sample tray was placed into the freezedryer chamber and placed on the freezedryer cooling shelf at a temperature of 20° C.

The freezedrying process involved the cooling of the freezedryer chamber and cooling shelf at a constant cooling rate (0.9° C./min), to the final temperature of freezing (40° C.). The shelf and chamber temperature was then held constant at the final temperature of freezing for 60 minutes. The shelf temperature was then ramped up to 0° C. over 160 minutes. The ice phase was then sublimated under a vacuum of approximately 200 mTorr at 0° C. for 17 hours.

The porous collagen/HA construct was then placed in a vacuum oven (Fisher IsoTemp 201, Fisher Scientific, Boston, Mass.) to crosslink the collagen via a dehydrothermal crosslinking process. The scaffolds were placed in the vacuum oven at a temperature of 120° C. under a vacuum of 50 mTorr for 24 hours.

Example 3

400 ml of a 0.5 M acetic acid solution (pH 2.55) was prepared using distilled, deionised water (11.6 ml glacial acetic acid was added to 388.4 ml of distilled, deionized water). A WK1250 water cooling system (Lauda, Westbury, N.Y., USA) was used to cool a glass reaction vessel to a constant temperature of 4° C. for one hour. 1.8 gm of microfibrillar bovine tendon collagen (Collagen Matrix Inc., N.J., USA) was added to 320 ml of the 0.5 M acetic acid solution. This suspension was blended using an IKA Ultra Turrax T18 overhead blender (IKA Works Inc., Wilmington, N.C.) at 15,000 rpm for 90 minutes at 4° C.

40 ml of the acetic acid solution was mixed with hydroxyapatite (HA) powder (Biotal, UK), specifically 50%, 100%, and 200%, by weight of collagen (0.9, 1.8, and 3.6 gm HA). A 10 ml aliquot of this acetic acid/HA solution was added to the collagen/acetic acid slurry in the cooled reaction vessel at 90 minutes. 10 ml aliquots (three in total) were subsequently added to the slurry every hour. After the final aliquot of acetic acid HA solution was added, the slurry was blended for a subsequent 60 minutes, leading to a total blend time of 330 minutes (five and a half hours). Once the blending stage was completed, the slurry was transferred to a clean, widenecked beaker and vacuum degassed at a pressure of approximately 4000 mTorr for an additional 60 minutes.

The scaffold was produced using a lyophilisation (freezedrying) process. A 67.5 ml aliquot of the collagen/HA slurry was placed in a walled freezedryer sample tray supplied by the freezedryer manufacturer (VirTis Co., Gardiner, N.Y., USA) and made from 304 grade stainless steel. The inner sample tray dimensions were 127 mm wide×127 mm length× 38 mm height. The tray base plate thickness is 3 mm. The sample tray was placed into a freezedryer chamber and placed on the freezedryer cooling shelf at a temperature of 20° C.

The freezedrying process involved the cooling of the freezedryer chamber and cooling shelf at a constant cooling rate (0.9° C./min), to the final temperature of freezing (40° C.). The shelf and chamber temperature was then held constant at the final temperature of freezing for 60 minutes. The shelf temperature was then ramped up to 0° C. over 160 minutes. The ice phase was then sublimated under a vacuum of approximately 200 mTorr at 0° C. for 17 hours to produce the porous collagen/HA scaffold.

The porous collagen/HA construct was then placed in a vacuum oven (Fisher IsoTemp 201, Fisher Scientific, Boston, Mass.) to crosslink the collagen via a dehydrothermal crosslinking process. The scaffolds were placed in the vacuum oven at a temperature of 120° C. under a vacuum of 50 mTorr for 24 hours.

Example 4

400 ml of a 0.5 M acetic acid solution (pH 2.55) was prepared using distilled, deionised water (11.6 ml glacial acetic acid was added to 388.4 ml of distilled, deionized water). A WK1250 water cooling system (Lauda, Westbury, N.Y., USA) was used to cool a glass reaction vessel to a constant temperature of 4° C. for one hour. 1.8 gm of microfibrillar bovine tendon collagen (Collagen Matrix Inc., N.J., USA) was added to 320 ml of the 0.5 M acetic acid solution. This suspension was blended using an IKA Ultra Turrax T18 overhead blender (IKA Works Inc., Wilmington, N.C.) at 15,000 rpm for 90 minutes at 4° C.

40 ml of the acetic acid solution was mixed with hydroxyapatite (HA) powder (Biotal, UK), specifically 50%, 100%, and 200%, by weight of collagen (0.9, 1.8, and 3.6 gm HA). A 10 ml aliquot of this acetic acid/HA solution was added to the collagen/acetic acid slurry in the cooled reaction vessel at 90 minutes. 10 ml aliquots (three in total) were subsequently added to the slurry every hour. After the final aliquot of acetic acid HA solution was added, the slurry was blended for a subsequent 60 minutes, leading to a total blend time of 330 minutes (five and a half hours). Once the blending stage was completed, the slurry was transferred to a clean, widenecked beaker and vacuum degassed at a pressure of approximately 4000 mTorr for an additional 60 minutes.

The scaffold was produced using a lyophilisation (freezedrying) process. A 67.5 ml aliquot of the collagen/HA slurry was placed in a walled freezedryer sample tray supplied by the freezedryer manufacturer (VirTis Co., Gardiner, N.Y., USA) and made from 304 grade stainless steel. The inner sample tray dimensions were 127 mm wide×127 mm length× 38 mm height. The tray base plate thickness is 3 mm. The sample tray was placed into a freezedryer chamber and placed on the freezedryer cooling shelf at a temperature of 20° C.

The freezedrying process involved the cooling of the freezedryer chamber and cooling shelf at a constant cooling rate (0.9° C./min), to the final temperature of freezing (40° C.). The shelf and chamber temperature was then held constant at the final temperature of freezing for 60 minutes. The shelf temperature was then ramped up to 0° C. over 160 minutes. The ice phase was then sublimated under a vacuum of approximately 200 mTorr at 0° C. for 17 hours to produce the porous collagen/HA scaffold.

The porous collagen/HA construct was then placed in a vacuum oven (Fisher IsoTemp 201, Fisher Scientific, Boston, Mass.) to crosslink the collagen via a dehydrothermal crosslinking process. The scaffolds were placed in the vacuum oven at a temperature of 120° C. under a vacuum of 50 mTorr for 24 hours.

Following the DHT crosslinking procedure, the scaffolds were chemically crosslinked using Ethyl-3-[3-dimethylaminopropyl]carbodiimide hydrochloride (EDAC) as the crosslinking agent. EDAC at a concentration of 6 mmol EDAC per gram of scaffold was mixed in a 5:2 molar ratio with N-Hydroxysuccinimide (EDAC:NHS=5:2). Scaffolds were immersed in this EDAC/NHS solution and incubated for 2 hours at room temperature. Subsequently scaffolds were rinsed twice using phosphate buffered saline (PBS) and incubated in PBS for two hours using an orbital shaker to agitate the PBS.

Characterisation of Composite Scaffolds

For the purpose of this study, all fabricated collagen/HA scaffolds were compared against a control scaffold made of collagen, fabricated using the standard protocol used within this research laboratory, specifically in 0.5M acetic acid solution and lyophilised at a constant cooling rate to a final freezing temperature of 40° C.

1. Mechanical Stiffness

Figure 1:
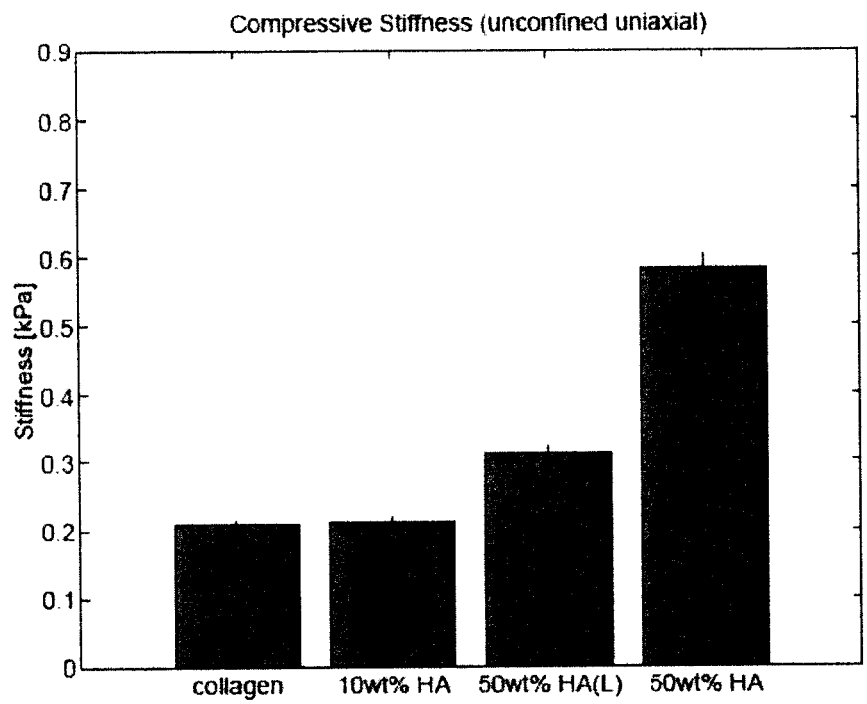
FIG. 1: Non-EDAC crosslinked scaffold compressive stiffness as a function of scaffold type. (collagen=collagen control scaffold mixed in 0.05M acetic acid, 10 wt % HA=collagen+10 wt % HA mixed in 0.05M acetic acid, 50 wt % HA(L)=collagen+50 wt % HA mixed in 0.1M acetic acid, 50 wt % HA=collagen+50 wt % HA mixed in 0.5M acetic acid).

To ensure survival once implanted into a bone defect, a bone graft substitute must possess sufficient intrinsic strength to withstand the forces it is subjected to through load bearing within the affected defect site. The ability to custom fabricate an osteoconductive bone graft substitute with sufficient intrinsic strength to allow implantation into a loadbearing defect was the primary goal of this study. Through the use of composite technology, an extremely biocompatible collagen-based construct is combined with the stronger ceramic hydroxyapatite to develop a bone graft substitute with all of the advantages of both materials with none of their disadvantages. All tests were conducted on scaffolds hydrated with phosphate buffered saline (PBS) solution. Compression testing of scaffold samples was carried out using a Zwick mechanical testing machine fitted with a 5-N load cell. Samples of 8 mm diameter (4 mm high) were cut from the sheets using a leather punch sharpened by a round metal file. The samples were then pre-hydrated with phosphate buffered saline (PBS) one hour prior to testing in a 24-well culture plate. The testing protocol consisted of two cycles: a precondition cycle and a test cycle. For both cycles a preload of 0.15 mN was applied and the position was held for one minute. This force was selected as it was low enough (0.5% of the load at 10% strain) to ensure contact with the sample without compressing the sample before the test. The position of the upper platen at this preload was used to measure the height of the scaffold. Hydrated scaffolds were placed on a dry platen which was then submerged prior to lowering the upper platen. Care was taken to insure that no bubbles were trapped between the upper platen and the scaffold. For preconditioning, the samples were loaded to 5%. For testing, the scaffolds were loaded to 10% and unloaded. A strain rate of 10% per minute was used. After testing the diameter of the samples was measured at three separate locations using a Vernier calipers. The modulus was defined as the slope of a linear fit to the stress-strain curve over 2-5% strain FIG. 1 shows the effect of adding HA to the non-EDAC crosslinked scaffold on compressive stiffness. The addition of 50 wt % HA was found to significantly increase the compressive stiffness measured by mechanical testing in unconfined compression. An increase in compressive stiffness of nearly 300% was seen relative to collagen scaffold product controls. Of particular interest was the effect of acetic acid concentration on the efficiency of HA incorporation within the construct. This is believed to explain the relatively small increase in stiffness by incorporating 10 wt % HA in the standard collagen slurry without increasing the acetic acid concentration accordingly. In conclusion, with as little as 50 wt % HA added, a greater than three fold increase in stiffness is achieved and by small adjustments to the acetic acid concentration, maximum gains in construct stiffness can be achieved with the addition of relatively small amounts of HA. Consequently, this will allow significant increases in the proportion of HA added by altering the initial acetic acid concentration accordingly in future studies.

Figure 2:
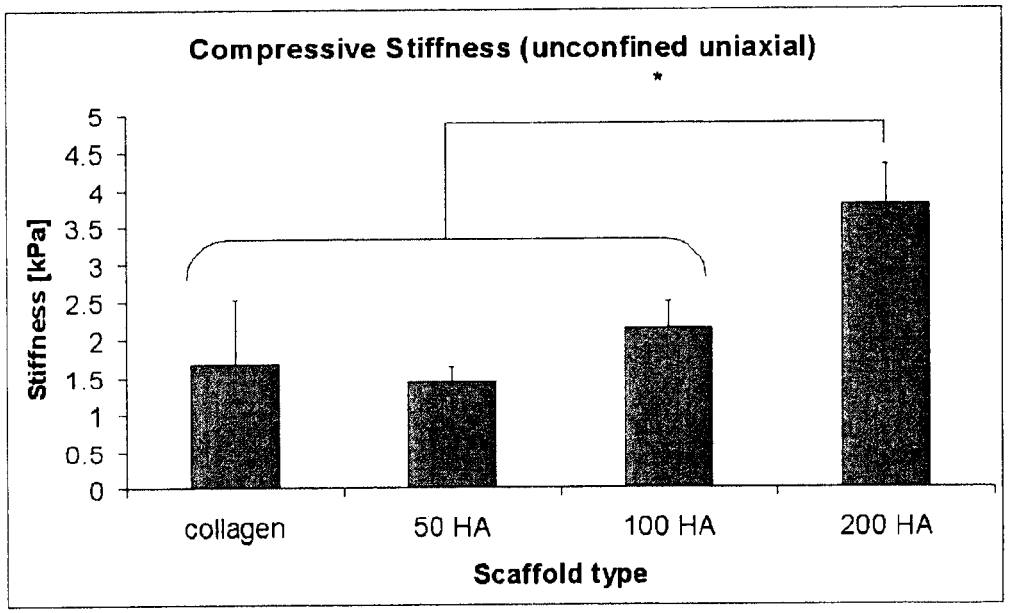
FIG. 2: EDAC crosslinked scaffold compressive stiffness as a function of scaffold type. (collagen=EDAC crosslinked collagen control scaffold mixed in 0.5M acetic acid, 50 HA=EDAC crosslinked collagen+50 wt % HA mixed in 0.5M acetic acid, 100 HA=EDAC crosslinked collagen+100 wt % HA mixed in 0.5M acetic acid, 200 HA=EDAC crosslinked collagen+200 wt % HA mixed in 0.5M acetic acid).

FIG. 2 shows the effect of adding HA to the EDAC crosslinked scaffold on compressive stiffness. The baseline scaffold, collagen, increases in stiffness from 0.2 kPa in FIG. 1 to about 1.5 kPa in FIG. 2. Addition of HA still increases the stiffness of the scaffolds as intended but at lower amounts of HA, such as 50 wt % HA, the effect of the EDAC crosslinking overshadows this. However, at 200 wt % HA, a significant increase in stiffness is seen as before. The addition of all amounts of HA was shown to significantly improve biocompatibility aspects of the crosslinked scaffolds and these are discussed in sections 5 and 7 below.

2. Invention Porosity

Figure 3:
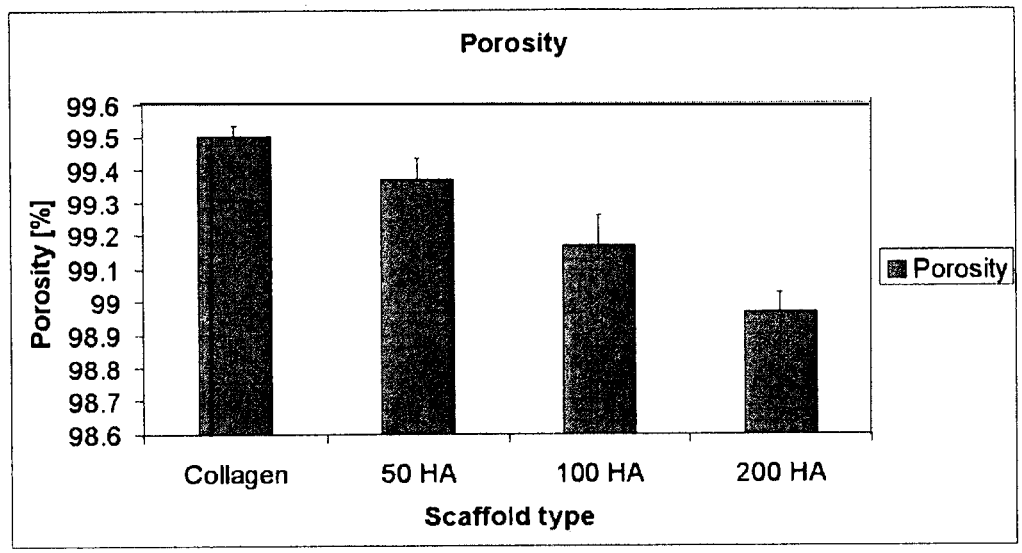
FIG. 3: Scaffold porosity as a function of scaffold type. (collagen=Non-EDAC crosslinked scaffold collagen control scaffold mixed in 0.5M acetic acid, 50 HA=Non-EDAC crosslinked scaffold collagen+50 wt % HA mixed in 0.5M acetic acid, 100 HA=Non-EDAC crosslinked scaffold collagen +100 wt % HA mixed in 0.5M acetic acid, 200

The porosity of a porous scaffold is a measure of the proportion of the scaffold volume composed of open, porous space expressed as a percentage. In simpler terms, it is the percentage pore volume of a porous construct. A high scaffold porosity is required for diffusion of nutrients/waste materials to/from cells both in vitro and in vivo. One of the main constraints in the development of engineered tissue scaffolds has been the issue of core degradation, arising from lack of nutrient delivery and waste removal from the centre of the construct. As a result, constructs often fail once implanted due to avascular necrosis in the centre of the scaffold. One of the big advantages of the collagen-based scaffolds of the present invention is their high porosity. Scaffold porosity was determined by the precise measurement of a dry 8 mm, 4 mm deep scaffold sample using a mass balance. Using the formula for the volume of a cylinder, $\pi r^2 h$, the density of each sample was calculated by dividing the mass by the volume. Porosity was calculated using the formula $100-[100(\rho_{scaffold}/\rho_{material})]$ where $\rho_{scaffold}$ is the density of a given sample and $\rho_{material}$ is the weighted density of the scaffold constituents (i.e. $\rho_{10\ wt\ \%\ HAScaffold} = [m_{collagen} + m_{10\ wt\ \%\ HA}]/[m_{collagen}/\rho_{collagen} + m_{10\ wt\ \%\ HA}/\rho_{10\ wt\ \%\ HA}])$ The addition of HA to the constructs resulted in a decrease in scaffold porosity but this was negligible in absolute terms as can be seen in FIG. 3. Therefore, the scaffolds of the invention incorporate HA into the construct while retaining a very high porosity to improve cellular migration into the centre of the scaffold to encourage subsequent cell proliferation. This was shown to be true in the in-vivo animal study data shown below.

Specifically, our range of porosities within scaffolds actually produced ranges from 99.5% for pure collagen down to 99% for the 200 wt % HA scaffolds.

3. Mineral Structure

The distribution of mineral particles throughout the scaffolds is a difficult parameter/attribute to quantify. It is an attribute that is much easier to visualize and therefore, a range of values to protect is difficult to define. It was visualized using two different methods. The first was microCT which is shown in FIG. 6 below. The microCT scanner used in this analysis uses X-rays to detect mineralised tissue. Consequently, FIG. 6 shows only the mineral particles within a 100 wt % HA scaffold. Knowing that the collagen is not visible, one can see that the mineral particles are completely and evenly distributed throughout the scaffold. Given that the scaffold is 99% empty, this image shows conclusive evidence that the HA is intimately associated with the collagen fibres. FIG. 7 shows a 2-dimensional slice of the same scaffold illustrating the distribution from another viewpoint.

FIGS. 8 and 9 illustrate the distribution of mineral particles throughout a 50 wt % HA scaffold using a distinct imaging tool, Scanning Electron Microscopy (SEM). Both images show the same region of interest within a 50 wt % HA scaffold. FIG. 8 shows both phases of collagen and HA. The mineral particles are indistinguishable to the naked eye. However, using Energy dispersive X-ray Analysis, the mineral particle can be detected for the identical region of interest (ROI). This is shown in FIG. 9 as white pixels representing mineral particles. In conjunction with the microCT data, these images prove conclusively that the mineral particles are evenly and homogenously distributed throughout the scaffold and are intimately associated with the collagen struts.

4. Pore Interconnectivity

Pore interconnectivity is another important scaffold attribute that is very difficult to define quantitatively in scaffolds composed primarily of biological material. However, pore interconnectivity is strongly related to scaffold permeability. Permeability is discussed below but the conductivity of flow is dependant on porosity, pore size and pore interconnectivity together. Consequently, permeability gives an indication of pore interconnectivity when pore size and porosity are defined.

SEM images of scaffolds of the invention are provided to illustrate the extremely high levels of pore interconnectivity which can be easily seen. FIG. 10 shows a 50 wt % HA scaffold at 10 times magnification and the obviously interconnected pore structure at the surface. This has been shown to be identical using thin sections taken from such samples. FIG. 11 shows the same 50 wt % scaffold at 100 times magnification. This image illustrates the pore interconnectivity. At this magnification, the pore structure is conclusively interconnected.

5. In-Vitro Bioactivity

The effect of the addition of HA to the collagen scaffold was assessed by quantifying the proliferation of MC3T3E1 osteoblasts in the scaffolds after 7, 14, 21 and 28 days incubation. The addition of HA to the scaffolds was found to have no detrimental effect on cellular activity. In fact, the opposite was found to be true at 28 days post seeding. Increasing the proportion of HA to 200 wt % HA was found to encourage cell proliferation even further than the control pure collagen scaffold. FIG. 4 shows the absolute cell numbers retained on the scaffolds.

As can be seen the 50 wt % HA scaffolds were retained a significantly lower number of cells due to empirical restrictions. Consequently, FIG. 4 does not give the best indication of bioactivity. Consequently, FIG. 5 illustrates the net mean cell number left within the scaffold types at 28 days. A net decrease of 0.5 million in cell proliferation is seen in the pure collagen constructs (approximately 20% decrease), which is not unsurprising given that the pure collagen construct is favourable but not optimized for osteoblast cells. However, the addition of 50 wt %, 100 wt % and 200 wt % HA results in a increased cellular proliferation of approximately 500%, 50% and 30% respectively (FIG. 4).

6. Invention Permeability

The permeability of a porous scaffold is essentially the flow conductivity under pressure through that porous medium. A high scaffold permeability is essential for long term viability of the scaffold in vivo as it allows cells to migrate to the scaffold centre and facilitates vascularisation in vivo. The 50 wt %, 100 wt % and 200 HA scaffolds exhibited a significantly increased mean tissue permeability relative to the control collagen scaffolds. This was a surprising but positive finding of this study as it shows that the addition of HA actually aids the flow of fluid throughout the scaffold. It is believed that this increase in flow conductivity through the porous scaffold is due to the increased scaffold rigidity. The empirical protocol used to quantify scaffold permeability is described in detail in reference [5] (O'Brien et al, 2007, Section 2.2, pages 7-10).

7. In-vivo Animal Trial

A small animal trial was carried out to determine the potential of this invention to encourage osteogenesis and mineralisation of a critically sized defect in bone. Nine Wistar rats were used during the trial. A critically sized defect was created in the rat calvaria. One animal was left with an empty defect as a control. The other eight animals were split into groups. Specifically, four of the defects were filled with 50 wt % HA scaffolds, two of which were seeded with rat mesenchymal stem cells (MSC) cells and two of which that were left unseeded. This was to investigate the potential of tissue engineered versus off the shelf scaffold types. The remaining four sample defects were filled with 200 wt % HA scaffolds and once again, these four were split evenly between seeded and unseeded scaffolds. After 28 days within the rat calvaria, the animals were sacrificed and the calvarial bones were removed. These were process and analysed using microCT to investigate the presence of scaffold within the defect and to observe the effect of scaffold types on the healing process, osteogenesis and mineralised matrix production. The figures in the following sections show 2-dimensional slices taken from the empty defect rat. Slices were coronal sections through the calvarial bone. The defects were 5 mm in diameter and perfectly circular. The sections shown in the microCT data are represented in the schematic below in FIG. 13.

Empty Defect (FIG. 14)

The empty defect animal data showed the defect was filled in with soft fibrous tissue as part of the healing process. This was expected and has been seen in previously conducted animal trials within our tissue engineering group. At some points throughout the defect after the 28 day trial, small particles of dense material were observed within the empty defect but these were seldom observed and not sufficiently dense to indicate significant healing within the empty defect sample. Examples of these are shown in the microCT X-ray images shown below.

50 wt % Seeded 1 (FIG. 15)

The 50 wt % HA cell-seeded scaffolds showed more promising results. These scaffolds were seeded with rat mesenchymal stem cells prior to implantation. As can be seen from the representative microCT x-ray images below, small heterogeneous pockets of mildly mineralized material were seen not only at the periphery of the defect-bone interface but also in the centre of the scaffolds. There were a significantly higher number of instances of these pockets of mineralization seen relative to the empty defect data and they appeared to be brighter in their intensity relative to the instances seen in the empty defect.

50 wt % Seeded 2 (FIG. 16)

Our second cell seeded 50 wt % HA scaffold showed much improved results relative to the first cell seeded 50 wt % HA scaffold and consequently the empty defect. Significant instances of heavily mineralised tissue were seen at points throughout the scaffold-filled defect. This was especially evident at the periphery of the scaffold-bone interface. The level of mineralisation was not high as that seen in the surrounding bone but was very similar. This can be seen as the nearly identical intensity levels of the mineralised tissue seen within the scaffold-filled defect and that of the surrounding bone.

200 wt % Seeded 1 (FIG. 17)

The first cell-seeded 200 wt % HA scaffold showed significantly improved results compared with the 50 wt % HA scaffolds. At nearly every point examined throughout the defect, significant levels of mineralisation were seen from the periphery of the defect all the way into the centre of the scaffold-filled defect. In this sample, the mineralisation level was not as high as that of the surrounding bone tissue indicated by the relative difference in the image intensity of the mineralised particles within the scaffold-filled defect.

200 wt % Seeded 2 (FIG. 18)

The second cell-seeded 200 wt % HA scaffold showed significantly improved results compared with all previous scaffolds. At a significant number of areas examined throughout the defect, significant levels of mineralisation were seen from the periphery of the defect all the way into the centre of the scaffold-filled defect. Unlike the first 200 wt % HA cell-seeded scaffolds, the mineralised tissue formed was not particulate in nature but was continuous across the scaffold-filled defect. Most interestingly, this continuous mineralisation was seen at the widest part of the defect. In this sample, the mineralisation level was nearly identical to that of the surrounding bone tissue indicated by the similar image intensity of the mineralised material within the scaffold-filled defect.

50 wt % Unseeded 1 (FIG. 19)

The cell-free scaffold-filled defect results for the 50 wt % HA scaffolds were very similar to the cell-seeded 50 wt % HA scaffolds. Significantly mineralised tissue was seen throughout the scaffold-filled defects but was not continuous in nature. However, the intensity of the mineralised tissue was marginally greater than that seen in the cell-seeded samples. This was seen in all cell unseeded samples that follow and indicated that a cell-free construct may perform better in vivo.

50 wt % Unseeded 2 (FIG. 20)

This 50 wt % HA cell-unseeded sample showed similar results to all other 50 wt % HA samples. After the 28 day trial, evidence of the beginning of scaffold mineralisation was seen at both the periphery and the centre of the scaffold-filled defect but the mineralised tissue was not continuous. However, the intensity of the mineralised particles indicated a mineralisation similar to that of the surrounding bone.

200 wt % Unseeded 1 (FIG. 21)

As seen in the 200 wt % HA cell-seeded samples, the unseeded 200 wt % HA sample showed significant levels of mineralisation at the periphery and the centre of the scaffold-filled defect at a significant number of areas throughout the defect. This mineralised tissue was continuous in nature unlike that seen in the 50 wt % HA samples.

200 wt % Unseeded 2 (FIG. 22)

As seen in the previous 200 wt % HA cell-unseeded sample, this unseeded 200 wt % HA sample showed significant levels of mineralisation at the periphery and the centre of the scaffold-filled defect at a significant number of areas throughout the defect. This mineralised tissue was continuous in nature unlike that seen in the 50 wt % HA samples.

The invention is not limited to the embodiments herein described. As such, the three embodiments of the invention described herein represent a small proportion of the total number of scaffold variants possible using the same core fabrication protocol. Either the constituents themselves or specific embodiment stages or process steps can be varied to produce a varied range of constructs, optimised for application specific use. The variations possible include;

Acetic acid concentration: The concentration of the acetic acid within the initial collagen slurry can be altered to suit specific applications. Increasing the concentration encourages a more rapid and homogenous integration of the HA particles within the blending slurry. Additionally, this concentration also has a significant effect on both the mechanical properties and the biocompatability of the scaffold. These effects are discussed in detail in the "Invention Characterisation" Section above. Suitably, the acetic acid concentration can be varied between 0.05M and 5M.

Collagen Quantity: The collagen quantity can be varied within the initial collagen slurry. Increasing the collagen quantity results in an increased mechanical stiffness of the resulting scaffold. This also has a significant effect on scaffold biocompatability. Suitably, the collagen quantity can vary from 0.5 g/L up to 50 g/L of acetic acid solution (1/10 and 10 times standard collagen concentration respectively).

Hydroxyapatite Quantity: The quantity of HA can be varied within a specified range relative to the proportion of collagen within the scaffold slurry prior to manufacture. Specifically, the quantity of HA can suitably vary from 10 to 1000 weight percent of the quantity of collagen used. Increasing the HA content was found to significantly increase the mechanical stiffness of the manufactured scaffold.

Hydroxyapatite Type: The present invention can be manufactured using both sintered, unsintered, and other forms of the HA powder.

Hydroxyapatite Addition: Both the HA aliquot volume and injection interval can be varied to facilitate mixing of the two primary constituent of the slurry. Generally, the injection interval can be varied from 30 minutes up to 240 minutes. Additionally, the aliquot volume can suitably be varied from 1 ml up to 100 ml. Such freedom facilitates optimisation of any particular invention embodiment.

Hydroxyapatite Particle Size: Typically, the HA particle size can be varied from 10 nm up to 100 μm to suit specific applications.

Final Freezing Temperature: The final freezing temperature reached during the freezedrying process determines the mean pore size within the manufactured scaffolds. This final freezing temperature can be varied to produce scaffolds with various mean pore sizes specific to a specific application or cell type. Suitably, the final freezing temperature can be varied from −10° C. down to −70° C.

Freezing Interface: The freezing interface placed between the embodiment slurry and the freezedryer cooling shelf can be varied. The type of freezing interface affects heat energy transmission to/from the slurry/scaffold and can alter the pore structure of the final scaffold. Four main options are available, specifically a walled vessel of defined interface made of either metal (1), plastic (2), a thin polymeric Membrane (3) or no interface (4).

Freezing Rate: The freezing rate determines the rate of ice crystal nucleation within the collagen/HA slurry during the freezedrying process and controls the homogeneity of the pore formation process. The cooling rate is varied to optimise the freezing process for the various types of interfaces available between the slurry and the freezedryer cooling shelf (e.g. metal, plastic, none). Typically, the freezing rate can be varied from 0.01° C./min up to 10° C./min.

Annealing: An annealing stage an be employed during the freezedrying process and allows the creation of pores with an average diameter significantly greater than pore sizes attainable by varying the final freezing temperature alone. The annealing time can be varied from 15 minutes to 36 hours. The longer the annealing time, the larger the final average pore size.

Scaffold Crosslinking Method: The crosslinking method can be one of a possible number of techniques, either dehydrothermal or chemical in nature. Additionally, both techniques can be employed consecutively. Specific crosslinking options include glutaraldehyde, carbodiimides (EDAC), microbial transglutaminase (mTgase), dehydrothermal crosslinking (DHT) and ultraviolet radiation (UV).

Scaffold Crosslinking Temperature/Concentration: The freezedried scaffold collagen can be crosslinked via dehydrothermal means to increase the scaffold mechanical stiffness. The crosslinking temperature can be varied from 105° C. up to 180° C. with a corresponding increase in embodiment stiffness. Additionally, when using chemical crosslinking methods, the concentration of the crosslinking solution can be varied to alter the extent of chemical crosslinking.

Scaffold Crosslinking Duration: The crosslink exposure time can also be varied to alter the extent of the crosslinking process throughout the scaffold. This can be varied between 24 and 120 hours to alter the final mechanical specification of the scaffold.

REFERENCES

[1] Tancred D. C., Carr A. J., and McCormack B. A. Development of a new synthetic bone graft. Journal of Materials Science: Materials in Medicine, 9(12):819-823, 1998.

[2] Dong J. K., Luthy H., Wohlwend A., and Scharer P. Heatpressed ceramics: technology and strength. International Journal of Prosthodontics, 5(1):9-16, 1992.

[3] Bailey A. J., Light N. D., and Atkins E.D.T. Chemical crosslinking restrictions on models for the molecular organisation of the collagen fibre. Nature, 288:408-410, 1980.

[4] Yannas I. V. Tissue and Organ Regeneration in Adults. New York: Springer, 2001.

[5] O'Brien F. J., Harley B. A., Yannas I. V., and Gibson L. J. The effect of pore size on cell adhesion in collagen gag scaffolds. Biomaterials, 26:433-441, 2005.

[6] O'Brien, F. J.; Harley, B. A.; Waller, M. A.; Yannas, I. V; Gibson, L. J and Prendergast, P. J. (2007) The effect of pore size on permeability and cell attachment in collagen scaffolds for tissue engineering. Technology and Healthcare Invited Article (15):3-17.

What is claimed is:

1. A collagen/hydroxyapatite (HA) composite scaffold comprising a homogenous distribution of hydroxyapatite within a porous, collagen matrix, wherein the ratio of HA to collagen ranges from 1:10 (w/w) to 50:10 (w/w), and wherein composite scaffold has a porosity of at least 97% (v/v) and a compressive stiffness of at least 0.4 KPa, wherein the composite scaffold further comprising a cell.

2. The collagen/hydroxyapatite (HA) composite scaffold of claim 1, wherein the composite scaffold comprises at least $1 \times 10^6$ cells per 500 mm$^3$ volume of scaffold.

3. The collagen/hydroxyapatite (HA) composite scaffold of claim 1, wherein the cells are osteoblasts.

4. The collagen/hydroxyapatite (HA) composite scaffold of claim 1, wherein the composite scaffold is characterised by a level of proliferation of MC3T3 osteoblasts in the scaffold at 28 days incubation minus the level at 7 days of at least $0.5 \times 10^6$ cells.

5. The collagen/hydroxyapatite (HA) composite scaffold of claim 1, wherein the composite scaffold is selected from the group consisting of: an osteoconductive bone implant, a tissue engineering implant, a maxillofacial bone graft substitute, a dental bone graft substitute, a cartilage defect repair implant, and a osteochondral defect repair implant.

6. The collagen/hydroxyapatite (HA) composite scaffold of claim 1, wherein the composite scaffold has a porosity of at least 97% (v/v).

7. The collagen/hydroxyapatite (HA) composite scaffold of claim 1, wherein the composite scaffold has a homogenous pore size.

8. The collagen/hydroxyapatite (HA) composite scaffold of claim 1, wherein the composite scaffold is cross-linked and has a compressive stiffness of at least 1.0 kPa.

9. The collagen/hydroxyapatite (HA) composite scaffold of claim 1, wherein the scaffold is cross-linked and has a compressive stiffness of at least 3.0 kPa.

10. The collagen/hydroxyapatite (HA) composite scaffold of claim 1, wherein the composite scaffold is characterized by having a flow conductivity under pressure through the scaffold of at least $1 \times 10^{-10}$ m$^4$/Ns.

11. The collagen/hydroxyapatite (HA) composite scaffold of claim 1, wherein the ratio of HA to collagen ranges from 5:10 (w/w) to 30:10 (w/w).

12. The collagen/hydroxyapatite (HA) composite scaffold of claim 1, wherein the ratio of HA to collagen ranges from 10:10 (w/w) to 30:10 (w/w).

13. The collagen/hydroxyapatite (HA) composite scaffold of claim 1, wherein the HA is in form of particles.

14. The collagen/hydroxyapatite (HA) composite scaffold of claim 12, wherein HA has a particle size of from 10 nm to 100 μm.

15. The collagen/hydroxyapatite (HA) composite scaffold of claim 1, wherein the composite scaffold is obtained by a process comprising the steps of mechanically mixing collagen and HA in an acidic solution to form a homogenous suspension of collagen and HA in an acidic solution, freezing the suspension at a constant cooling rate until a final freezing temperature of between −10° C. and −70° C. is reached, and heating the frozen suspension to a sublimation temperature where an ice phase in the frozen suspension is sublimated under vacuum for a suitable period of time to produce the composite scaffold, wherein the ratio of HA to collagen in the suspension ranges from 1:10 (w/w) to 50:10 (w/w), and the amount of collagen in the suspension is from 3 g/L to 8 g/L (w/w), wherein the homogenous suspension of collagen/HA is formed by the steps of forming an acidic homogenous suspension of collagen, and subsequently adding the HA to the collagen suspension under conditions of mixing to ensure homogenous distribution of the HA within the collagen suspension, in which the HA is added in the form of an acidic HA suspension.

* * * * *